US011041018B2

(12) United States Patent
Ponomarev et al.

(10) Patent No.: US 11,041,018 B2
(45) Date of Patent: Jun. 22, 2021

(54) AGGLUTINATION OF GANGLIOSIDES FOR TREATING ALZHEIMER'S DISEASE

(71) Applicant: The Chinese University of Hong Kong, Hong Kong (CN)

(72) Inventors: Eugene Ponomarev, Hong Kong (CN); Marina Dukhinova, Krasnogorsk (RU); Tatyana Veremeyko, Koltsovo (RU); Andrew L. M. Chan, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 16/412,082

(22) Filed: May 14, 2019

(65) Prior Publication Data

US 2020/0017578 A1 Jan. 16, 2020

Related U.S. Application Data

(60) Provisional application No. 62/682,596, filed on Jun. 8, 2018.

(51) Int. Cl.

| *A61K 9/00* | (2006.01) |
| *A61P 25/28* | (2006.01) |
| *C07K 14/435* | (2006.01) |
| *C07K 16/18* | (2006.01) |
| *C07K 14/47* | (2006.01) |
| *C07K 14/37* | (2006.01) |

(52) U.S. Cl.
CPC ............ *C07K 16/18* (2013.01); *A61K 9/0019* (2013.01); *A61P 25/28* (2018.01); *C07K 14/37* (2013.01); *C07K 14/43504* (2013.01); *C07K 14/43509* (2013.01); *C07K 14/43536* (2013.01); *C07K 14/4726* (2013.01)

(58) Field of Classification Search
CPC .............. C07K 14/37; C07K 14/43509; C07K 14/43536; C07K 14/4726; C07K 14/43504; A61P 25/28
See application file for complete search history.

(56) References Cited

U.S. PATENT DOCUMENTS

2005/0027110 A1\* 2/2005 Russell ................ A61K 38/185
530/397

OTHER PUBLICATIONS

Ariga T et al. (2013) PLoS ONE, 8(5): e63326. (Year: 2013).\*
Ariga T. (2017) Mol. Neurobiol. 54, 623-638. (Year: 2017).\*
Koutsouraki E et al. (2014) J. Alzheimer's Dis. 42, S163-S166. (Year: 2014).\*
Yanagisawa K. (2011) J. Neurochem. 116, 806-812. (Year: 2011).\*
Bernardo, et al. "Elimination of GD3 synthase improves memory and reduces amyloid-β plaque load in transgenic mice." Neurobiology of aging 30, No. 11 (2009): 1777-1791.
Dukhinova, et al. "Fresh evidence for major brain gangliosides as a target for the treatment of Alzheimer's disease." Neurobiology of aging 77 (2019): 128-143.
Kakio, et al. "Cholesterol-dependent formation of GM1 ganglioside-bound amyloid β-protein, an endogenous seed for Alzheimer amyloid." Journal of Biological Chemistry 276, No. 27 (2001): 24985-24990.
Malchiodi-Albedi, at al. "Lipid raft disruption protects mature neurons against amyloid oligomer toxicity." Biochimica et Biophysica Acta (BBA)—Molecular Basis of Disease 1802, No. 4 (2010): 406-415.
Wang, et al. "Reduction in cholesterol and sialic acid content protects cells from the toxic effects of β-amyloid peptides." Journal of Biological Chemistry 276, No. 45 (2001): 42027-42034.
Dukhinova, et al., "Platelets mediate protective neuroinflammation and promote neuronal plasticity at the site of neuronal injury," Brain, Behavior, and Immunity, vol. 74, pp. 7-27 (2018).
Kopeikina, et al., "Platelets promote epileptic seizures by modulating brain serotonin level, enhancing neuronal electric activity, and contributing to neuroinflammation and oxidative stress," Progress in Neurobiology, vol. 188, 101783, 21 pages (2020).
Starossom, et al., "Platelets Play Differential Role During the Initiation and Progression of Autoimmune Neuroinflammation," Circ Res., vol. 117(9), pp. 779-792 (2015).
Sotnikov, et al., "Platelets Recognize Brain-Specific Glycolipid Structures, Respond to Neurovascular Damage and Promote Neuroinflammation," PLOS ONE, vol. 8, Issue 3, e58979, 19 pages (2013).

\* cited by examiner

*Primary Examiner* — Kimberly Ballard

(74) *Attorney, Agent, or Firm* — Kilpatrick Townsend & Stockton LLP

(57) ABSTRACT

The present invention provides for novel compositions and methods for treating a neurodegenerative disease such as Alzheimer's Disease.

5 Claims, 22 Drawing Sheets

Specification includes a Sequence Listing.

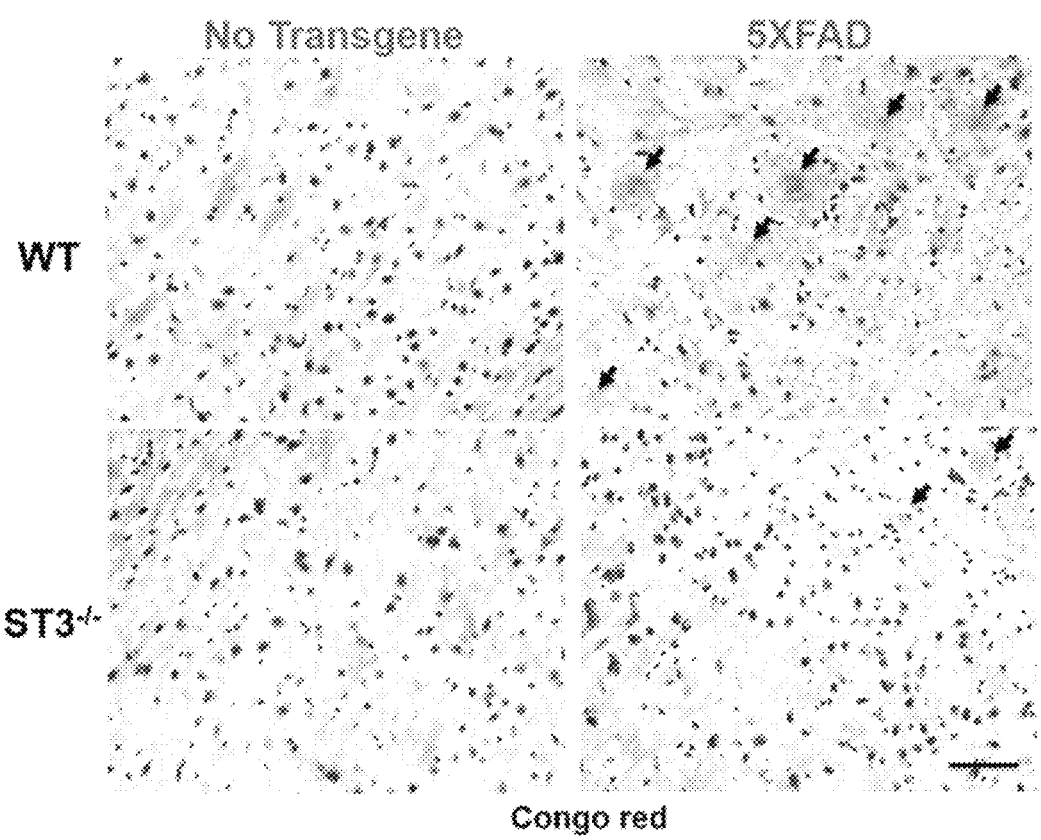
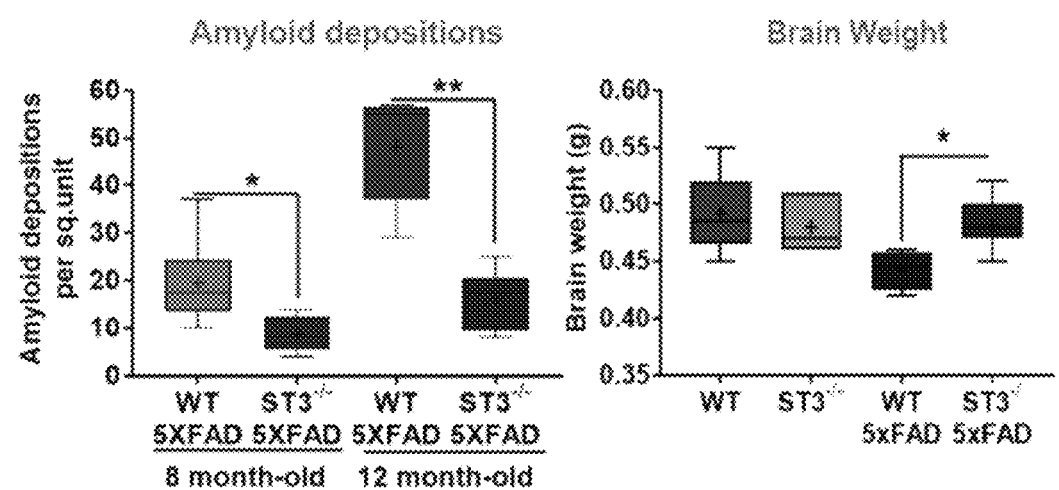
FIGURE 1A
FIGURE 1B
FIGURE 1C

FIGURE 3A
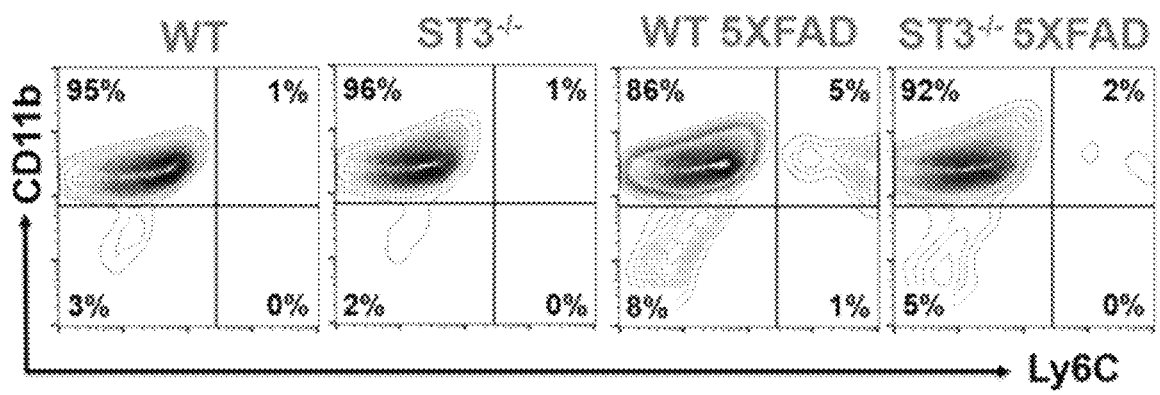
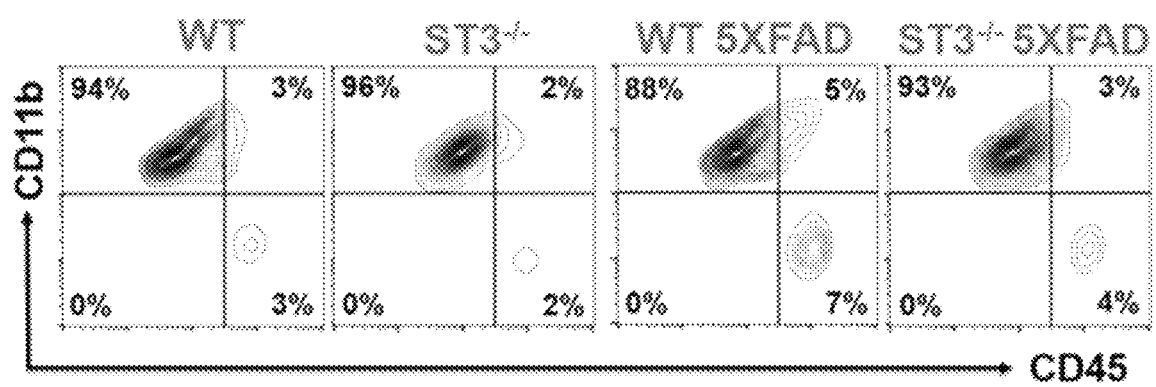
FIGURE 3B
FIG. 4

FIGURE 4A
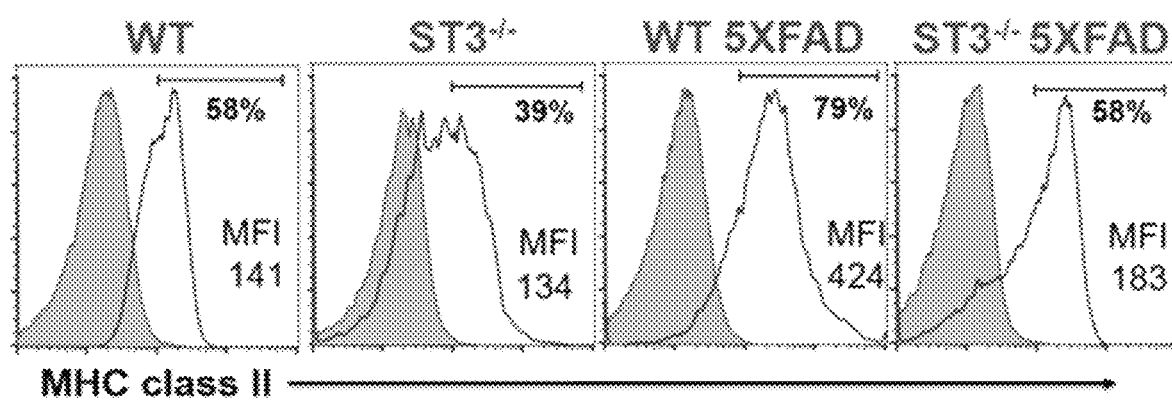
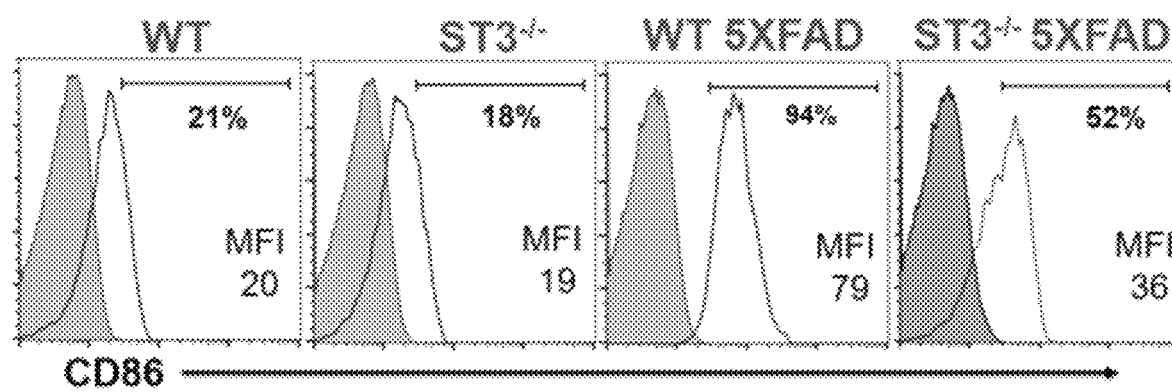
FIGURE 4B

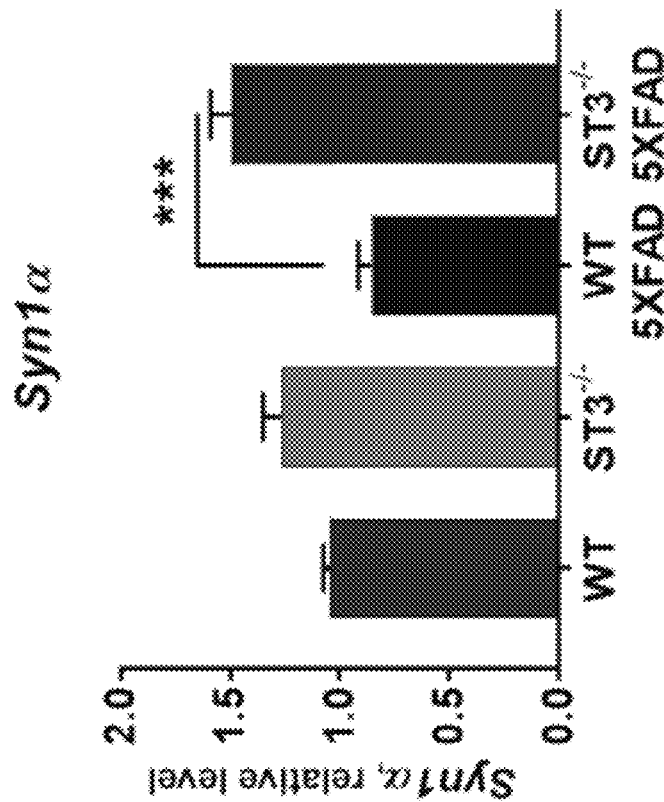
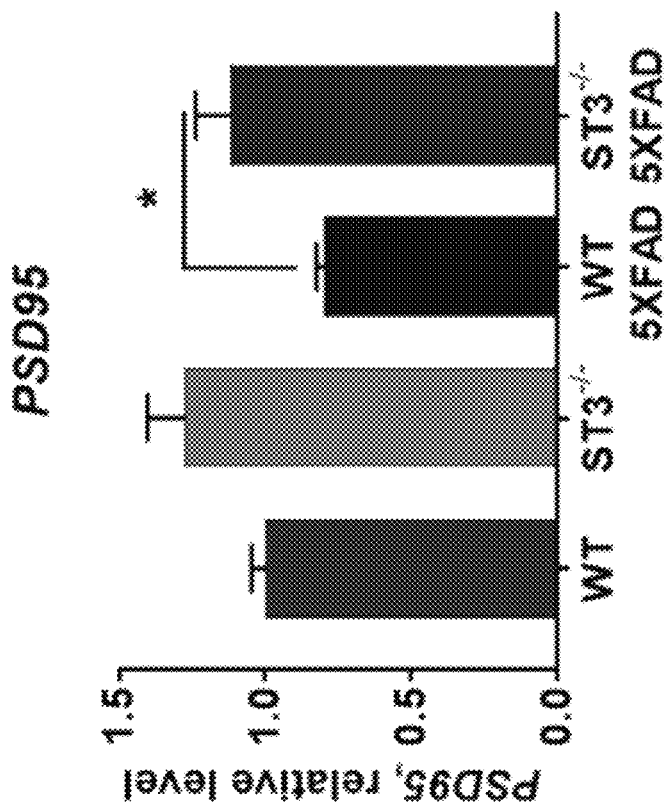
FIGURE 6C
FIGURE 6D

FIGURE 7D
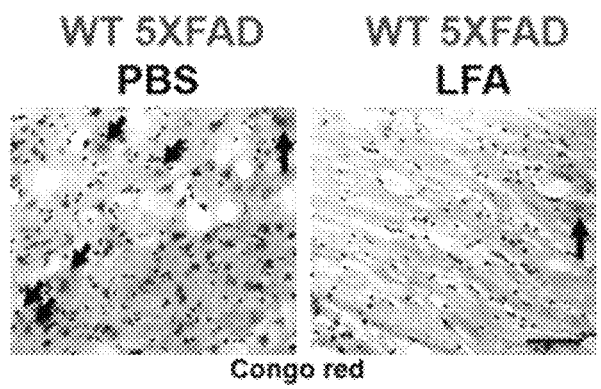
FIGURE 7E
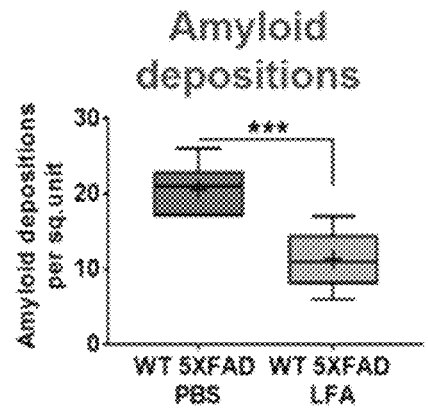
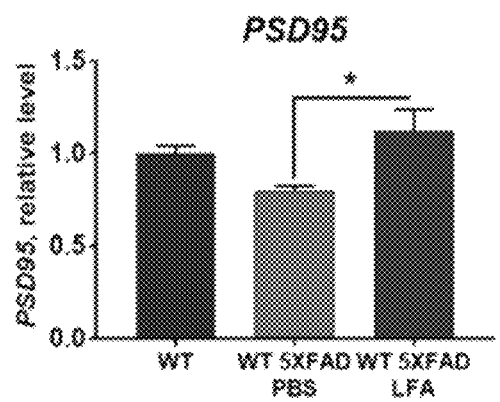
FIGURE 7F
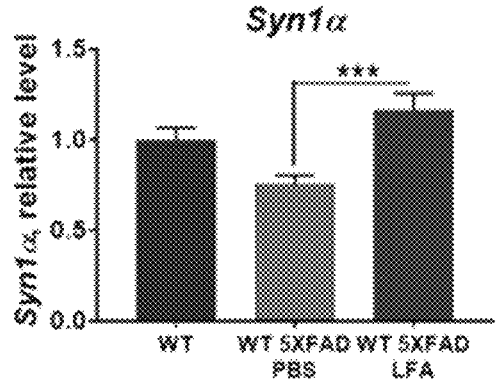
FIGURE 7G

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tctgtgcgag aggtagcaga                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 2
aagcactccg tgaactcctg                                                    20

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccgccagctg ccttc                                                         15

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgcagcccaa tgaccaaa                                                      18

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttccaggat gaggacatga gcac                                               24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcatcatccc atgagtcaca gagg                                               24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agccgatggg ttgtaccttg                                                    20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

-continued

```
gtgggtgagg agcacgtagt c                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgaccacag tccatgccat c                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagcttcccg ttcagctctg                                                20
```

AGGLUTINATION OF GANGLIOSIDES FOR TREATING ALZHEIMER'S DISEASE

RELATED APPLICATIONS

This application claims priority to U.S. Patent Application No. 62/682,596, filed Jun. 8, 2018, the contents of which are hereby incorporated by reference in the entirety for all purposes.

REFERENCE TO A SEQUENCE LISTING SUBMITTED IN COMPUTER READABLE FORMAT

The instant application contains a Sequence Listing which has been filed electronically in ASCII format and is hereby incorporated by reference in its entirety. Said ASCII copy, created on Sep. 24, 2019, is named 80015-1136567_(025110US)_SL.txt and is 2,567 bytes in size.

BACKGROUND OF THE INVENTION

Alzheimer's disease (AD) is the most common form of dementia affecting the aging population. Its pathology involves accumulation of amyloid plaques and neurofibrillary tangles in the patients' brain. Cognitive impairment, regarded as an early manifestation of AD, is believed to be attributable to disruptions of synaptic functions. At the present time, there are an estimated 50 million AD sufferers worldwide, and the number is expected to increase to at least 76 million by the year 2030 and over 130 million by the year 2050. AD is ranked No. 6 among the leading cause of all deaths in the United States, and ranked as high as $3^{rd}$ cause of deaths among the elderlies. Although AD symptoms typically begin to emerge in a patient's late 60s or 70s, early onset of AD can be seen among patients in their 40s or even late 30s. Currently there is no cure for AD, and AD patients invariably experience gradual deterioration over time until their death. The prevalence of AD and demands for AD patient treatment and maintenance have significant and profound socio-economic implications. In the US alone, the annual cost related to AD patient care is well over 600 billion dollars.

Accordingly, there exits a pressing need to develop new and effective methods and compositions for treating AD and other neurodegenerative disorders by alleviating the pertinent symptoms and/or delaying the onset of such symptoms. This invention fulfills this and other related needs.

BRIEF SUMMARY OF THE INVENTION

Alzheimer's disease (AD) is a systemic neurodegenerative disorder of the central nervous system (CNS) that have a high prevalence in the aging population worldwide. The disease is associated with synaptic distinction, brain atrophy, and progressive cognitive decline. Effective therapy for the disease is still not developed. A major hallmark of CNS pathology of AD includes extracellular depositions of polymerized aggregated fragments of amyloid-β (Aβ). Polymeric and oligomeric Aβ species contribute to neuronal toxicity with subsequent neuronal loss and neurodegeneration. In this study, the present inventors found that mice expressing human Aβ and deficient for certain carbohydrate structures in the brain do not develop amyloid depositions in the brain. Moreover, Aβ species did not interact with neurons and caused neither neuronal loss nor brain atrophy. Neuroinflammation was also significantly decreased in these mice. When mice expressing human Aβ and with intact brain carbohydrate structures were treated with specific lectin that binds to these carbohydrates, mice exhibited significant improvement in AD as determined by decreased amyloid depositions, a decrease in neuroinflammation, an increase in expression of synaptic markers, and significant improvement in the results of the cognitive test. Since similar carbohydrate structures are present in human brain, these results obtained in animal model are directly applicable for humans to develop new therapy of AD. Thus, this invention provides novel methods and compositions useful for treating a neurodegenerative disorder including AD, both prophylactically and therapeutically.

In the first aspect, the present invention provides a composition for use in the treatment of a neurodegenerative disorder such as Alzheimer's Disease. The composition comprises an effective amount of an agent capable of agglutinating sialylated gangliosides and at least one pharmaceutically acceptable excipient. For example, the agent may be a lectin with binding specificity for a sialic acid, e.g., *Limax flavus* agglutinin (LFA), *Limulus polyphemus* agglutinin (LPA), *Paecilomyes japonica* agglutinin (PJA), lobster agglutinin I, or *Penaeus monodin* lectin, or the agent may be an antibody (monoclonal or polyclonal antibody, preferably a humanized monoclonal antibody) against a ganglioside, especially a major brain ganglioside such as GM1, GM2, GM3, GD1a, GD3, GT1b, or GQ1b. In some embodiments, the composition is for use in the treatment of Alzheimer's Disease. In some embodiments, the composition is formulated for injection, such as intravenous, intramuscular, intraperitoneal, or subcutaneous injection. In some embodiments, the composition is formulated for oral ingestion. In some embodiments, the composition is formulated for nasal inhalation. For example, one or more pharmaceutically acceptable excipients that are particularly suitable for any one of the above-mentioned specific means of administration may be included in the composition. In some embodiments, the composition further comprises a second therapeutic agent effective for treating a neurodegenerative disorder.

In a related aspect, the present invention provides a novel use of a ganglioside-agglutinating agent for the manufacturing of a medicament useful for treating a neurodegenerative disorder as such Alzheimer's Disease. The medicament comprises an effective amount of ZL600 and a physiologically acceptable excipient. In some embodiments, the medicament is for treating Alzheimer's Disease. In some embodiments, the agent is a lectin with binding specificity for a sialic acid, e.g., *Limax flavus* agglutinin (LFA), *Limulus polyphemus* agglutinin (LPA), *Paecilomyes japonica* agglutinin (PJA), lobster agglutinin I, or *Penaeus monodin* lectin; or the agent is an antibody (a monoclonal or polyclonal antibody, preferably a humanized monoclonal antibody) specifically binding a ganglioside, especially a major brain ganglioside such as GM1, GM2, GM3, GD1a, GD3, GT1b, or GQ1b. In some embodiments, the medicament is formulated for injection (such as intravenous, intramuscular, intraperitoneal, or subcutaneous injection), for oral administration, or for nasal inhalation. For example, one or more pharmaceutically acceptable excipients that are particularly suitable for any one of the above-mentioned specific means of administration may be included in the medicament. In some embodiments, the medicament further comprises another therapeutic agent effective for treating a neurodegenerative disorder (e.g., Alzheimer's Disease). In some embodiments, the medicament is formulated and/or packaged in a dose form containing an effective amount of a ganglioside-agglutinating agent such as LFA for one administration.

In a second aspect, the present invention provides a method for treating a neurodegenerative disorder such as Alzheimer's Disease in a subject. The method includes the step of administering to the subject a composition containing an effective amount of a ganglioside-agglutinating agent. In some embodiments, the subject has received diagnosis of Alzheimer's Disease, or the subject has been deemed to have an increased risk of later developing Alzheimer's Disease, for example, due to family history or known genetic mutations. In some embodiments, the agent is a lectin with binding specificity for a sialic acid, e.g., *Limax flavus* agglutinin (LFA), *Limulus polyphemus* agglutinin (LPA), *Paecilomyes japonica* agglutinin (PJA), lobster agglutinin I, or *Penaeus monodin* lectin; in other embodiments, the agent is an antibody (a monoclonal or polyclonal antibody, preferably a humanized monoclonal antibody) specifically binding a ganglioside, especially a major brain ganglioside such as GM1, GM2, GM3, GD1a, GD3, GT1b, or GQ1b. In some embodiments, the administering step comprises injection of the composition, such as intravenous, intramuscular, intraperitoneal, or subcutaneous injection. In some embodiments, the administering step comprises oral ingestion of the composition. In some embodiments, the administering step comprises nasal inhalation of the composition. For example, one or more pharmaceutically acceptable excipients that are particularly suitable for any one of the above-mentioned specific means of administration may be included in the composition. In some embodiments, LFA is administered by intravenous injection in an amount of about 5-100 mg/kg patient body weight, for example, about 10-50 mg/kg patient body weight. In some embodiments, LFA is administered by intravenous injection in an amount of about 20 mg/kg patient body weight. In some embodiments, the subject is further administered an effective amount of a second therapeutic agent known to be effective for treating a neurodegenerative disorder such as Alzheimer's Disease.

In a third aspect, the present invention provides a kit for treating neurodegenerative disorders such as Alzheimer's Disease. The kit comprises a first container containing a pharmaceutical composition comprising an effective amount of a ganglioside-agglutinating agent. In some embodiments, the agent is a lectin with binding specificity for a sialic acid, e.g., *Limax flavus* agglutinin (LFA), *Limulus polyphemus* agglutinin (LPA), *Paecilomyes japonica* agglutinin (PJA), lobster agglutinin I, or *Penaeus monodin* lectin. In some embodiments, the agent is an antibody (a monoclonal or polyclonal antibody, preferably a humanized monoclonal antibody) specifically binding a ganglioside such as GM1, GM2, GM3, GD1a, GD3, GT1b, or GQ1b. The composition may be formulated for administration by injection (such as intravenous, intramuscular, intraperitoneal, or subcutaneous injection), by oral ingestion, or by nasal inhalation. For example, one or more pharmaceutically acceptable excipients that are particularly suitable for any one of the above-mentioned specific means of administration may be included in the composition. In some embodiments, the kit further comprises a second container containing a second therapeutic agent known to be effective for treating a neurodegenerative disorder such as Alzheimer's Disease. In some embodiments, the kit further comprises informational material providing instructions on administration of the pharmaceutical composition.

BRIEF DESCRIPTION OF THE DRAWINGS

FIGS. 1A-1C. Analysis of amyloid plaque burden in the brain cortex and the brain weight of aged WT, ST3$^{-/-}$, WT 5XFAD, and ST3$^{-/-}$ 5 XFAD mice. (FIG. 1A) Brain histology sections of 8-month-old control WT, ST3$^{-/-}$, WT 5XFAD, and ST3$^{-/-}$ 5 XFAD mice were stained with Congo red and counterstained with hematoxylin as described in Materials and Methods. Amyloid depositions are indicated by arrows. Scale bar: 100 µm. (FIG. 1B) Quantitative analysis of plaque numbers in the brain cortical area of 8- and 12-month-old WT 5XFAD and age-matched ST3$^{-/-}$ 5 XFAD mice. (FIG. 1C) Quantitative analysis of wet brain weight of 8-month-old WT, ST3$^{-/-}$, WT 5XFAD, and ST3$^{-/-}$ 5 XFAD mice. The weight of each brain was measured on a laboratory scale after whole-body perfusion with PBS and subsequent dissection. Whisker plots with median and 10%/90% percentiles of 5-8 individual animals are shown in FIG. 1B and FIG. 1C (*, $p<0.05$; **, $p<0.01$). Mean values are indicated by "+" symbols.

(FIG. 2A) Brain histology sections of 8-month-old WT, ST3$^{-/-}$, WT 5XFAD, and ST3$^{-/-}$ 5 XFAD mice were prepared and stained for amyloid depositions with ThT-FITC (green), microglial cell marker Iba1 (red), and nuclear marker DAPI (blue) as described in Materials and Methods. Sites of co-localization of amyloid depositions and microglia (yellow) are marked with arrows. Scale bars: 100 µm (lower magnification) and 10 µm (higher magnification). (FIG. 2B) Quantitative analysis of Iba1$^+$ microglial cell covered area in brain cortical areas where amyloid depositions were evident for WT 5XFAD and ST3$^{-/-}$ 5 XFAD mice. (FIG. 2C) Quantitative analysis of the percentage of Iba1$^+$ microglia co-localized with ThT$^+$ amyloid depositions in the brain cortical areas where amyloid depositions were evident for WT 5XFAD and ST3$^{-/-}$ 5 XFAD mice. FIG. 2B and FIG. 2C show the analysis of sections from 3-4 animals with a total number of 15-20 section images. Whisker plots with median and 10%/90% percentiles of 15-20 images are shown (*, $p<0.05$; **, $p<0.01$). Mean values are indicated by "+" symbols.

FIGS. 3A-3D. Comparison of extent of infiltration of peripheral monocytes and lymphocytes in the brain cortex of WT 5XFAD and ST3$^{-/-}$ 5 XFAD mice. (FIG. 3A, FIG. 3B) Analysis of microglia activation and macrophage infiltration in the brains of 8-month-old WT, ST3$^{-/-}$, WT 5XFAD, and ST3$^{-/-}$ 5 XFAD mice. Mononuclear cells were isolated from the brain and analyzed for expression of CD11b, Ly6C, and CD45 by flow cytometry. (FIG. 3A) Representative contour-plots for expression of Ly6C (x-axes) and CD11b (y-axes) are shown. The quadrants distinguish populations of CD11b$^+$Ly6C$^-$ (microglia), CD11b$^+$Ly6C$^+$ (peripheral monocytes/macrophages), and CD11131Ly6C" and CD11b$^-$Ly6C$^+$ cells (both are lymphocytes). The percentage of each population is shown in the corner of each quadrant. (FIG. 3B) Representative contour-plots for expression of CD45 (x-axes) and CD11b (y-axes) are shown. The quadrants distinguish populations of CD11b$^+$CD45$^{low/int}$ (microglia), CD11b$^+$CD45 (peripheral monocytes/macrophages), CD11b$^-$ CD45$^-$ (contaminating astroglial cells), and CD11b$^-$CD45$^{hi}$ cells (lymphocytes). The percentage of each population is shown in the corner of each quadrant. (FIG. 3C, FIG. 3D) Quantitative analysis of percentages of CD11b$^+$Ly6C$^+$ peripheral monocytes/macrophages (FIG. 3C) and CD11b$^-$CD45$^{hi}$ lymphocytes (FIG. 3D). The data are representative of four experiments with a total number of 12-15 mice. Whisker plots with median and 10%/90% percentiles of 12-15 individual animals are shown (**, $p<0.01$). Mean values are indicated by "+" symbols.

FIGS. 4A-4D. Comparison of the expression levels of microglia activation markers MHC class II and CD86 in the brain cortex of WT 5XFAD and ST3$^{-/-}$ 5 XFAD mice. Analysis of microglia activation in the brain of 8-month-old WT, ST3$^{-/-}$, WT5xFAD, and ST3$^{-/-}$ 5 XFAD mice. Mononuclear cells were isolated from the brain and analyzed for expression of CD11b, Ly6C, CD45, MHC class II, and CD86 by five-color flow cytometry as described in Materials and Methods. Brain resident microglial cells were gated as CD11b$^+$CD45$^{low/int}$Ly6 C$^-$ and analyzed for the expression of activation markers MHC class II and CD86. (FIG. 4A-4B) Representative histograms for expressions of MHC class II (FIG. 4A) and CD86 (FIG. 4B) on CD11b$^+$CD45$^{low/int}$Ly6C$^-$ gated microglia are shown. The solid lines represent staining for MHC class II or CD86, and the dotted lines represent staining for isotype-matched controls. Percentages of positive cells are shown below linear gates and mean fluorescent intensity (MFI) values are shown in the bottom left corner of each histogram. (FIGS. 4AC-4D) Quantitative analysis of MFI levels for MHC class II (FIG. 4C) and CD86 (FIG. 4D) are shown. Whisker plots with median and 10%/90% percentiles of 5-12 individual animals are shown (**, p<0.01). Mean values are indicated by "+" symbols.

(FIG. 5A) Brains of 8-month-old WT, ST3$^{-/-}$, 5XFAD, and ST3$^{-/-}$ 5 XFAD were collected for histology analysis and stained with Cresyl violet dye as described in Materials and Methods. Representative images are shown. The centers of representative perivascular areas are indicated by "*" symbols. Scale bar: 100 μm. (FIG. 5B) Brain histology sections of 8-month-old WT, ST3" 5XFAD, and ST3$^{-/-}$ 5 XFAD mice were stained for neuronal marker (β3-tubulin; green), human APP (hAPP; red), and nuclei (DAPI; blue). Scale bar: 25 μm. (FIG. 5C, FIG. 5D) Quantification of the neuronal cell-covered (β3-tubulin$^+$; FIG. 5C) and amyloid-covered (hAPP$^+$; FIG. 5D) areas in the brain sections of WT, ST3$^{-/-}$, 5XFAD and ST3$^{-/-}$ 5XFAD mice. Whisker plots with median and 10%/90% percentiles of 4-5 individual animals are shown (**, p<0.01). Mean values are indicated by "+" symbols.

FIGS. 6A-6F. Comparison of the expression levels of pro-inflammatory cytokines IL-1β and TNF and synaptic markers PSD95 and Syn-1 in the brain cortex of WT 5XFAD and ST3$^{-/-}$ 5 XFAD mice. (FIGS. 6A-D) Analysis of mRNA expression levels of pro-inflammatory cytokines TNF (FIG. 6A) and IL-1β (FIG. 6B), and neuronal synaptic markers PSD95 (FIG. 6C) and Synapsin1A (FIG. 6D) in the brain of WT, ST3$^{-/-}$, WT 5XFAD, and ST3$^{-/-}$ 5 XFAD mice. The brains of 8-month-old WT, ST3$^{-/-}$, WT 5XFAD, and ST3$^{-/-}$ 5 XFAD mice were dissected after perfusion, mRNA was isolated and real-time RT PCR was performed as described in Materials and Methods. In (FIG. 6D-6F) means±S. E. of 3-4 individual animals are shown (*, p<0.05; *, p<0.001). (FIG. 6E, 6F) Comparison of cognitive abilities of 8-month-old WT, ST3$^{-/-}$, WT 5XFAD, and ST3$^{-/-}$ 5 XFAD mice by Barnes maze test. Over a 4-day period, mice were trained to perform the task and on day 5 the final trial was performed as described in Materials and Methods. The latency time was recorded during training on days 1-4 (FIG. 6E) and on the final trial on day 5 (FIG. 6F). In (FIG. 6E), mean±S.E. is shown for a group of 3-4 individual mice. In (FIG. 6F), whisker plots with median and 10%/90% percentiles of 3-4 individual animals are shown (*, p<0.001). Mean values are indicated by "+" symbols.

FIGS. 7A-7G. Effects of administration of sialic acid-specific lectin LFA into 6-month-old WT 5XFAD mice for 5 weeks on cognitive abilities, the number of amyloid plaques and the expression of synaptic markers. (FIG. 7A) Scheme of systemic administration of LFA lectin (20 mg/kg) into 6-month-old WT 5XFAD mice 3 times a week for 5 weeks following Barnes maze test and analysis of brain cortex for signs of AD pathology. (FIG. 7B, FIG. 7C) Comparison of cognitive abilities of 7-month-old WT 5XFAD mice treated with PBS or LFA for 5 weeks prior to Barnes maze test. Over a 4-day period, mice were trained to perform the task and on day 5 a final trial was performed as for FIG. 6. The latency time was recorded during training on days 1-4 (FIG. 7B) and on the final trial on day 5 (FIG. 7C). (FIG. 7D) Comparison of images of the brain cortical area of PBS- vs. LFA-treated WT 5xFAD mice. Brain sections were stained with Congo red to detect amyloid plaques as for FIG. 1 and representative images are shown. Amyloid depositions are indicated by arrows. Scale bar: 100 μm. (FIG. 7E) Quantification of amyloid plaque numbers in the brain cortical area of PBS- vs. LFA-treated WT 5XFAD mice is shown. Quantification was performed as for FIG. 1. (FIG. 7F, FIG. 7G) Analysis of mRNA expression levels of neuronal synaptic markers PSD95 (FIG. 7C) and Synapsin1A (FIG. 7F) in the brains of PBS- vs. LFA-treated 7-month-old WT 5XFAD mice. RNA isolation and real-time RT PCR was performed as for FIG. 6. In (FIG. 7B, FIG. 7F, FIG. 7G), mean±S.E. is shown for the group of 4-5 individual mice (*, p<0.05; , p<0.01; *, p<0.001). In (FIG. 7C, FIG. 7E), whisker plots with median and 10%/90% percentiles of 4-5 individual animals are shown (; , p<0.01; *, p<0.001). Mean values are indicated by "+" symbols.

(FIG. 8A, FIG. 8B) Analysis of mRNA expression levels of pro-inflammatory cytokines TNF (FIG. 8A) and IL-1β (FIG. 8B) in the brains of PBS- vs. LFA-treated 7-month-old WT 5XFAD mice. RNA isolation and real-time RT PCR was performed as for FIG. 6. (FIG. 8C-8E) Brain histology sections of PBS- vs. LFA-treated 7-month-old WT 5XFAD mice were prepared and stained for amyloid depositions with ThT-FITC (green), microglial cell marker Iba1 (red), and nuclear marker DAPI (blue) as in FIG. 2. Sites of co-localization of amyloid depositions and microglia (yellow color) are marked with arrows. Scale bars: 100 μm (lower magnification) and 10 μm (higher magnification). (FIG. 8D) Quantitative analysis of Iba1$^+$ microglial cell covered area in the brain cortical areas where amyloid depositions are evident. (FIG. 8E) Quantitative analysis of the percentage of Iba1$^+$ microglia co-localized with ThT$^+$ amyloid depositions in the brain cortical areas where amyloid depositions are evident. In (FIG. 8A, FIG. 8B), means±S. E. are shown for a group of 4-5 individual mice (*, p<0.05; ****, p<0.0001). In (FIG. 8D, FIG. 8E) the analysis of sections from three animals with a total number of 15-20 section images is shown. Whisker plots with median and 10%/90% percentiles of 15-20 images are shown (*, p<0.05; *, p<0.001; **, p<0.0001). Mean values are indicated by "+" symbols.

(FIG. 9A) Schematic diagram of amyloid plaque formation on the surface of neuronal cells in the brains of WT 5XFAD mice. Neuronal cells in WT 5XFAD mice overexpress mutated human APP695 proteins under a neuron-specific Thy1 promoter. Expressed full-length human transmembrane APP695 protein is cleaved by β-secretase and then by a γ-secretase complex to form short Aβ$_{1-40}$ and Aβ$_{1-42}$ peptides that aggregate and form amyloid depositions on the outer surface of neuronal plasma membrane. (FIG. 9B) Descriptions of five transgenes that are overexpressed in WT 5XFAD transgenic mice in neuronal cells under a neuron-specific Thy1 promoter. These five transgenes include three human APP695 genes with Swedish (K670N and M671L), Florida (I716V) and London (V7171) mutations and two human PS-1 genes with M146L and L286V mutations that form a γ-secretase complex. (FIG. 9C) Schematic diagram of neuronal lipid rafts. Neuronal lipid rafts are rigid detergent-resistant membrane domains that have high concentrations of glycolipids, sialylated glycolipids, transmembrane glycoproteins and intramembrane cholesterol. Synaptic areas of mature neurons are specially enriched with neuronal lipid rafts. (FIG. 9D) Schematic diagram comparing the spectrum of expression of various sialylated glycosphingolipids in WT vs ST3$^{-/-}$ (GM3-synthase) deficient mice. WT mice express all indicated gangliosides including major brain gangliosides GM1, GD1b, GD1a, GT1b, and GQ1b, all of which are highly expressed in mature neurons. ST3-deficient mice do not express major brain gangliosides but still express sialylated cisGM1 and GD1α. (FIG. 9E) Model of formation of amyloid depositions in WT 5XFAD, ST3$^{-/-}$ 5 XFAD and LFA-treated WT 5XFAD mice. WT 5XFAD mice have a large number of sialylated gangliosides GM1, GT1b and GQ1b within neuronal lipid rafts that have high ability to bind Aβ$_{1-40}$ and Aβ$_{1-42}$ peptides to form amyloid depositions. Sialic acid with α2.6 linkage to carbohydrate core is critical for the binding of Aβ$_{1-40}$ and Aβ$_{1-42}$ peptides to the neuronal lipid rafts. Thus, in the CNS of WT 5XFAD mice, the formation of amyloid depositions, increased neuroinflammation, downregulation of synaptic markers and a decline in cognitive abilities were observed. In ST3$^{-/-}$ 5 XFAD mice the number of sialylated gangliosides with α2.6 linkage to carbohydrate core was greatly reduced, leading to a significant reduction of amyloid depositions because Aβ$_{1-40}$ and Aβ$_{1-42}$ peptides do not efficiently bind to asialo-gangliosides or to cisGM1 and GD1α. Decreased levels of amyloid depositions in these mice resulted in a decrease in neuroinflammation, an increase in the expression of synaptic markers and improved cognitive ability. In WT 5XFAD mice treated with sialic acid-specific LFA, this lectin binds to sialic acid in neuronal lipid rafts and blocks the binding of amyloid peptides to neuronal plasma membranes, leading to substantial improvement in AD pathology with an observed phenotype similar to ST3$^{-/-}$ 5 XFAD mice with decreased neuroinflammation, increased expression of synaptic markers and improved cognitive abilities.

DEFINITIONS

Figure 2A:
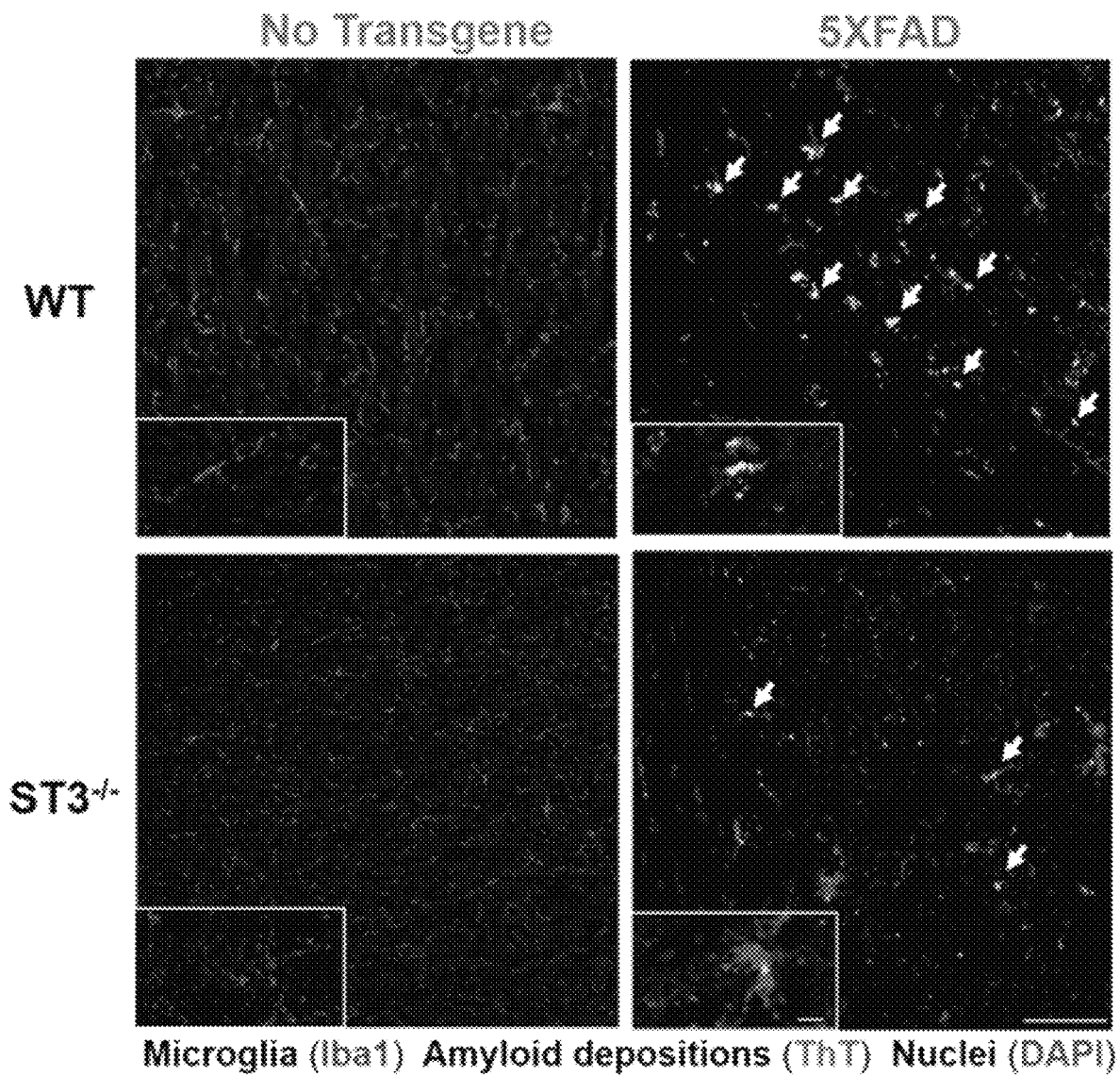
FIGS. 2A-2C. Comparison of the level of microglia activation in areas of amyloid depositions in the brain cortex of WT 5XFAD and ST3$^{-/-}$ 5 XFAD mice.

"Ganglioside" is a molecule composed of a glycosphingolipid (ceramide and oligosaccharide) with one or more sialic acids linked on the sugar chain. Sialic acids are the N- or O-substituted derivatives of neuraminic acid (e.g., n-acetylneuraminic acid, or NANA), a monosaccharide with a nine-carbon backbone. More than 60 gangliosides are known to date, including major brain gangliosides GM1, GM2, GM3, GD1a, GD1b, GD2, GD3, GT1b, and GQ1b as the more pertinent to this invention. The term "major brain gangliosides" include gangliosides GM1, GM2, GM3, GD1a, GD1b, GD2, GD3, GT1b, and GQ1b in human or mammalian brain that together constitute 97% of all brain gagngliosides.

The term "agglutinating" or "agglutination," as used herein, refers to a clumping or aggregation process by which particles, especially cells or macromolecules, bind to each other and form aggregates, clumps or clogs. One example of agglutination is cells or macromolecules "glued" or bind together by the action of an antibody or protein (such as lectin) that can specifically bind the cells or macromolecules. Clumps or clogs formed due to agglutination can be detected under microscope and/or by naked eyes. Molecular aggregates could be also detected by other methods such as receptor-ligand binding affinity assays. In this context, a "ganglioside-agglutinating agent" is a substance that is capable of binding and agglutinating a ganglioside under physiological conditions, e.g., in vivo or in vitro (for example, in cell culture).

The term "inhibiting" or "inhibition," as used herein, refers to any detectable negative effect on a target biological process, such as any one of neurodegenerative symptoms exhibited by a patient suffering from a neurodegenerative disorder including Alzheimer's Disease (AD). Typically, an inhibition of a neurodegenerative symptom is reflected in a decrease of at least 10%, 20%, 30%, 40%, 50%, 60%, 70%, 80%, 90% or higher, including 100% or complete elimination, of one or more hallmarks of a neurodegenerative disorder (e.g., AD) as described herein, when compared to a control not given the "inhibition" treatment, such as treatment by administration of small molecule therapeutics described herein. On the other hand, inhibition of a neurodegenerative symptom may also be manifested as increased cell survival (e.g., neuronal cell survival), demonstrated in an increase of at least 50%, 60%, 70%, 80%, 90%, 100%, 200%, 300%, 500% or more in the number or length of time of cell survival in the pertinent tissues (especially in the central nervous system or CNS) within the recipient body after the small molecule administration in comparison to a control that has not received the same treatment.

As used herein, the term "treatment" or "treating" includes both therapeutic and preventative measures taken to address the presence of a disease or condition or the risk of developing such disease or condition at a later time. It encompasses therapeutic or preventive measures for alleviating ongoing symptoms, inhibiting or slowing disease progression, delaying of onset of symptoms, or eliminating or reducing side-effects caused by such disease or condition. A preventive measure in this context and its variations do not require 100% elimination of the occurrence of an event; rather, they refer to a suppression or reduction in the likelihood or severity of such occurrence or a delay in such occurrence.

As used herein, the term "neurodegenerative disorder" includes, but is not limited to, the following conditions: (1) Diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, amyotrophic lateral sclerosis (ALS) and variants thereof, dentatorubral atrophy, olivo-pontocerebellar atrophy, paraneoplastic cerebellar degeneration, and dopamine toxicity; (2) Diseases affecting sensory neurons such as Friedreich's ataxia, diabetes, peripheral neuropathy, retinal neuronal degeneration; (3) Diseases of limbic and cortical systems such as cerebral amyloidosis, Pick's atrophy, Retts syndrome; (4) Neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of central nervous system (CNS) degeneration, corticobasal degeneration and progressive supranuclear palsy; (5) Pathologies associated with developmental retardation and learning impairments, Down's syndrome, and oxidative stress induced neuronal death; (6) Pathologies arising with aging and chronic alcohol or drug abuse including, for example, with alcoholism the degeneration of neurons in locus coeruleus, cerebellum, cholinergic basal forebrain; with aging degeneration of cerebellar neurons and cortical neurons leading to cognitive and motor impairments; and with chronic amphetamine abuse degeneration of basal ganglia neurons leading to motor impairments; (7) Pathological changes resulting from focal trauma such as stroke, focal ischemia, vascular insufficiency, hypoxic-ischemic encephalopathy, hyperglycemia, hypoglycemia, closed head trauma, or direct trauma; and (8) Pathologies arising as a negative side-effect of therapeutic drugs and treatments (e.g., degeneration of cingulate and entorhinal cortex neurons in response to anticonvulsant doses of antagonists of the N-methyl-D-aspartate (NMDA) class of glutamate receptor).

"Alzheimer's Disease" or AD is a chronic neurodegenerative disease with a progressive pattern of cognitive and functional impairment. Although certain genetic mutations have been identified as contributing to the risk of developing AD, the exact cause of the disease remains largely undetermined. On the other hand, the symptoms of AD are well-recognized: initially a patient experiences difficulty in remembering recent events, i.e., short-term memory loss. As the disease develops, the patient further exhibits symptoms such as difficulties with language, disorientation, mood swings, loss of motivation, inability of self-care, and behavioral problems. As the patient's condition declines, he typically begins to withdraw from family and society. Gradually, the patient's bodily functions are lost, which ultimately leads to death. Although the pace of disease progression can vary, the typical life expectancy of an AD patient is around three to nine years following diagnosis. AD usually affects patients aged 65 years or older, with about 5% of AD diagnosis made in patients younger than 65.

A "patient" or "subject" receiving the composition or treatment method of this invention is a human, typically adult human, of any age, gender, and ethnic background, who has been diagnosed to suffer from a neurodegenerative disorder such as AD exhibiting one or more pertinent symptoms, or who has been identified as having increased risk of developing a neurodegenerative disorder (e.g., AD) due to family history and/or known genetic mutations even though the subject may not yet develop any symptoms of the disorder. Typically, a patient diagnosed with or at risk of developing a neurodegenerative disorder is at least 60 or 70 or 80 years of age; in some early onset cases, however, such a patient may be between 50 and 60 years old, or younger than 50 years of age, or still in his 40s or even late 30s.

The term "effective amount," as used herein, refers to an amount that produces therapeutic effects for which a substance is administered. The effects include the prevention, correction, or inhibition of progression of the symptoms of a disease/condition and related complications to any detectable extent, e.g., one or more of the hallmarks of a neurodegenerative disorder (e.g., AD). The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The term "about" when used in reference to a given value denotes a range encompassing ±10% of the value.

"*Limax flavus* agglutinin (LFA)" refers to a specific protein within the generic term of lectins, which are carbohydrate-binding proteins that specifically recognize or bind sugar moieties. Typically possessing no enzymatic activity, lectins are involved in cell adhesion and agglutination as well as the formation of glycoconjugates. Extracted from the slug, *Limax flavus*, LFA is a lectin with a specificity for sialic acid, see, e.g., Miller and Cannon (1984) *Prog. Clin. Biol. Res.* 157:31-41; and Knibbs et al. (1993) *J. Bio. Chem.* 268(5):18724-18531. *Limulus polyphemus* hemagglutinin (LPA), from the hemolymph of the Atlantic horseshoe crab *Limulus polyphemus*, is another lectin with a sialic acid-binding specificity similar to that of LFA. Other similar lectins include *Paecilomyes japonica* agglutinin (PJA), lobster agglutinin I, and *Penaeus monodin* lectin.

A "pharmaceutically acceptable" or "pharmacologically acceptable" excipient is a substance that is not biologically harmful or otherwise undesirable, i.e., the excipient may be administered to an individual along with a bioactive agent without causing any undesirable biological effects. Neither would the excipient interact in a deleterious manner with any of the components of the composition in which it is contained.

The term "excipient" refers to any essentially accessory substance that may be present in the finished dosage form of the composition of this invention. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

An "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) Fundamental Immunology, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology.

Further modification of antibodies by recombinant technologies is also well known in the art. For instance, chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient. On the other hand, "humanized" antibodies combine an even smaller portion of the non-human antibody with human components. Generally, a humanized antibody comprises the hypervariable regions, or complementarity determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al. (1986) Nature 321:522-525).

Thus, the term "antibody," as used herein, also includes antibody fragments either produced by the modification of whole antibodies or antibodies synthesized de novo using recombinant DNA methodologies (e.g., single chain Fv, a chimeric or humanized antibody).

The term "consisting essentially of," when used in the context of describing a composition containing an active ingredient, refer to the fact that the composition does not contain other ingredients possessing any similar or relevant biological activity, whereas one or more inactive ingredients such as physiological or pharmaceutically acceptable excipients may be present in the composition. For example, a composition consisting essentially of an agent (for instance, LFA) effective for treating a neurodegenerative disorder such as AD is a composition that does not contain any other agents that may have any prophylactic or therapeutic effect on the neurodegenerative disorder (e.g., AD).

DETAILED DESCRIPTION OF THE INVENTION

I. Introduction

Although it has been shown that ganglioside GM1 plays an important role in the binding of amyloid fragments to neuronal cells, the exact role of neuronal gangliosides in Alzheimer's disease (AD) pathology remains unclear. To understand the role of sialylated gangliosides in AD pathology in vivo, st3gal5-deficient (ST3$^{-/-}$) mice that lack the major brain gangliosides GM1, GD3, GT1b and GQ1b were crossed with 5XFAD transgenic mice that overexpress three mutant human amyloid proteins AP695 and two presenilin PS1 genes. It was discovered that, in contrast to WT 5XFAD mice, ST3-deficient 5XFAD mice have a significantly reduced burden of amyloid depositions in the brain. In addition, ST3$^{-/-}$ 5 XFAD mice have a low level of neuroinflammation as determined by microglia activation and leukocyte infiltration. Moreover, ST3$^{-/-}$ 5 XFAD mice did not exhibit substantial neuronal loss, brain atrophy and a decrease in expression of synaptic markers PSD95 and Syn1. Finally, ST3$^{-/-}$ 5XFAD mice performed significantly better in a cognitive test than WT 5XFAD mice, which was comparable with normal WT mice without 5XFAD transgenes. Treatment of WT 5XFAD mice with the sialic acid-specific lectin Limax flavus agglutinin (LFA) resulted in substantial improvement of AD pathology to a level similar to the phenotype observed in ST3$^{-/-}$ 5 XFAD mice, as determined by decreased amyloid deposition; a decrease in neuroinflammation; an increase in the expression of synaptic markers; and significant improvement in the results of the cognitive test. These findings highlight an important role for sialylated gangliosides as a target for the treatment of AD.

While a possible role of brain gangliosides in AD pathology has been previously indicated, there were conflicting observations (see, e.g., Oikawa et al., 2009 and Bernardo et al., 2009). The study disclosed herein is the first definitive report that agents capable of agglutinating sialylated gangliosides can alleviate AD symptoms in an AD animal model. This invention therefore provides a new method for treating neurodegenerative disorders such as AD, where one or more neurodegenerative symptoms are resulted from or excerbated by the actions of β-amyloid deposits (Aβ) and/or PSD-95. A patient is suitable for receiving the treatment method of this invention is a person who has been diagnosed with a neurodegenerative disorders such as AD and exhibits some pertinent symptoms, or who has not yet been given the diagnosis of a neurodegenerative disorder and does not exhibit any symptoms but has been deemed to be at increased risk of developing a neurodegenerative disorder such as AD at a later time due to family history and/or known genetic risks. In some cases, the suitable subject may be younger than 60 or 65, e.g., in the age range of about 30-40, 40-50, 50-60, or 60-64. Among the known genetic risk factors, genes encoding the amyloid precursor protein (APP) and presenilins 1 and 2 have been found to exhibit a high rate of mutation in familia AD. Another genetic risk for AD is mutations in the TREM2 (triggering receptor expressed on myeloid cells 2) gene, which are reported as increasing the likelihood of one developing AD by 3-5 fold. One further known genetic risk factor is the inheritance of the ε4 allele of the apolipoprotein E (APOE) gene, with about 40-80% AD patients have at least one copy of this allele. More recent genome-wide association studies (GWAS) have found 19 areas in genes that appear to affect the risk of developing AD. These genes include: CASS4, CELF1, FERMT2, HLA-DRB5, INPP5D, MEF2C, NME8, PTK2B, SORL1, ZCWPW1, S1C24A4, CLU, PICALM, CR1, BIN1, MS4A, ABCA7, EPHA1, and CD2AP. Thus, genetic analysis of these relevant genomic loci can aid identification of subjects at a heightened risk for AD that may be suitable recipients for the treatment method of the present invention.

The diagnosis of AD is based on well-established clinical criteria taking into consideration a patient's medical history, family history, and behavioral observations to detect the presence of neurological and neuropsychological features characteristic for AD combined with the absence of indications for alternative conditions. Advanced medical imaging techniques including computed tomography (CT), magnetic resonance imaging (MRI), single-photon emission computed tomography (SPECT), and positron emission tomography (PET) can be used to help make AD diagnosis and/or exclude other conditions such as cerebral pathology or subtypes of dementia.

Assessment of intellectual functioning including memory testing can be further to diagnose the disease and ascertain the severity/progression of the disease. Diagnostic criteria have been established and standardized for practising physicians. For example, the National Institute of Neurological and Communicative Disorders and Stroke (NINCDS) and the Alzheimer's Disease and Related Disorders Association (ADRDA, now known as the Alzheimer's Association) established the most commonly used NINCDS-ADRDA Alzheimer's Criteria for diagnosis in 1984, which were extensively updated in 2007. These criteria require that the presence of cognitive impairment, and a suspected dementia syndrome, be confirmed by neuropsychological testing for a clinical diagnosis of possible or probable AD. Eight cognitive domains are most commonly impaired in AD: memory, language, perceptual skills, attention, constructive abilities, orientation, problem solving, and functional abilities. These domains are equivalent to the NINCDS-ADRDA Alzheimer's Criteria as listed in the Diagnostic and Statistical Manual of Mental Disorders (DSM-IV-TR) published by the American Psychiatric Association. Utlizing these established criteria, patients can be identified with a reasonable accuracy and reliability, thus deemed appropriate recipients for the treatment methods of this invention.

As an additional aspect of the invention, new therapeutic agents for AD treatment may be identified based on their capability of causing ganglioside agglutination, i.e., being ganglioside-agglutinating agents. Although known ganglioside-agglutinating agents are lectins or anti-ganglioside antibodies, compounds of essentially any chemical structure could potentially serve as ganglioside-agglutinating agents and therefore as an anti-AD therapeutic agents. Screening assays may be designed for the identification of new ganglioside-agglutinating agents by virtue of detecting the formation of ganglioside clumps under physiological conditions in an in vivo or in vitro assay.

II. Pharmaceutical Compositions and Administration

The present invention also provides pharmaceutical compositions comprising an effective amount of a ganglioside-agglutinating agent for treating a neurodegenerative disorder such as AD in both prophylactic and therapeutic applications. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, intranasal, or intraperitoneal. The preferred routes of administering the pharmaceutical compositions are local delivery to an organ or tissue (e.g., via intravenous injection or intranasal administration) at daily doses of about 0.1-20, about 0.14-14 g, about 0.5-5 g, about 1-3 g, e.g., about 1-2 or about 1.4 g, of the ganglioside-agglutinating agent for a 70 kg adult human per day. The appropriate dose may be administered in a single daily dose or as divided doses presented at appropriate intervals, for example as two, three, four, or more subdoses per day.

For preparing pharmaceutical compositions containing an ganglioside-agglutinating agent, one or more inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., a ganglioside-agglutinating agent such as LFA. In tablets, the active ingredient is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of a ganglioside-agglutinating agent with encapsulating material as a carrier providing a capsule in which the active compound (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., LFA) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., LFA) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing the ganglioside-agglutinating agent can be administered for prophylactic and/or therapeutic treatments. In therapeutic applications, compositions are administered to a patient already suffering from a neurodegenerative disorder, e.g., AD, in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 0.05 g to about 5 g of the ganglioside-agglutinating agent per day for a 70 kg patient, with dosages of from about 0.05 g to about 1 g of the agent per day for a 70 kg patient being more commonly used.

In prophylactic applications, pharmaceutical compositions containing ZL006 are administered to a patient susceptible to or otherwise at risk of developing a neurodegenerative disorder (for example, AD) in an amount sufficient to delay or prevent the onset of the symptoms. Such an amount is defined to be a "prophylactically effective dose." In this use, the precise amounts of the ganglioside-agglutinating agent again depend on the patient's state of health and weight, but generally range from about 0.05 g to about 5 g of the agent for a 70 kg patient per day, more commonly from about 10 mg to about 1 g for a 70 kg patient per day.

Single or multiple administrations of the compositions can be carried out with dose levels and pattern being selected by the treating physician. In any event, the pharmaceutical formulations should provide a quantity of a ganglioside-agglutinating agent sufficient to effectively ameliorate, reduce, or reverse the relevant symptoms in the patient or delay the onset of the symptoms, either therapeutically or prophylactically.

III. Additional Therapeutic Agents

Additional known therapeutic agent or agents may be used in combination with a ganglioside-agglutinating agent such as LFA in the practice of the present invention for the purpose of treating a neurodegenerative disorder such as AD. In prophylactic or therapeutic applications, one or more of these previously known therapeutic agents can be administered to patients concurrently with an effective amount of the ganglioside inhibitor either together in a single composition or separately in two or more different compositions.

For example, drugs currently approved for use to treat the cognitive deficit aspect of AD include four acetylcholinesterase inhibitors, tacrine, rivastigmine, galantamine and donepezil, and one NMDA receptor antagonist, memantine. Huperzine A, a substance derived from a plant called Chinese club moss, has also been used for treating AD for reducing memory loss. In some AD patients, especial those experience distinct behavioral symptoms, are often given atypical antipsychotics for reducing aggression and psychosis associated with the disease. Lastly, a number of anti-Aβ antibodies, especially humanized anti-Aβ monoclonal antibodies, have been tested in clinical trials and shown varying degrees of effectiveness. One or more of these agents can be used along with the ganglioside-agglutinating agent such as LFA in a combination therapy scheme for treating AD.

IV. Kits

The invention also provides kits for treating a neurodegenerative disorder such as Alzheimer's Disease according to the method of the present invention. The kits typically include a first container that contains a pharmaceutical composition comprising a ganglioside-agglutinating agent that is therapeutically effective to ameliorate the symptoms of the neurodegenerative disorder (e.g., AD) and at least one pharmaceutically acceptable excipient, optionally with an additional container that contains a pharmaceutical composition comprising another therapeutically effective compound for ameliorating the symptoms of the neurodegenerative disorder (such as those described in the last section or otherwise known in the pertinent research field). In some variations of the kits, a single container may contain a pharmaceutical composition comprising two or more of compounds effective for treating a neurodegenerative disorder (e.g., AD) such as LFA and those described in the last section or otherwise known in the pertinent research field. The kits may further include informational material providing instructions on how to dispense the pharmaceutical composition(s), including description of the type of patients who may be treated (e.g., human patients who have received a diagnosis of a neurodegenerative disorder (e.g., AD) or have been deemed as with high risk of developing the neurodegenerative disorder including AD, for example, due to a strong propensity indicated by a family history or genetic risk factor), the schedule (e.g., dose and frequency) and route of administration, and the like.

EXAMPLES

The following examples are provided by way of illustration only and not by way of limitation. Those of skill in the art will readily recognize a variety of non-critical parameters that could be changed or modified to yield essentially the same or similar results.

Introduction

Figures 9A, 9B:
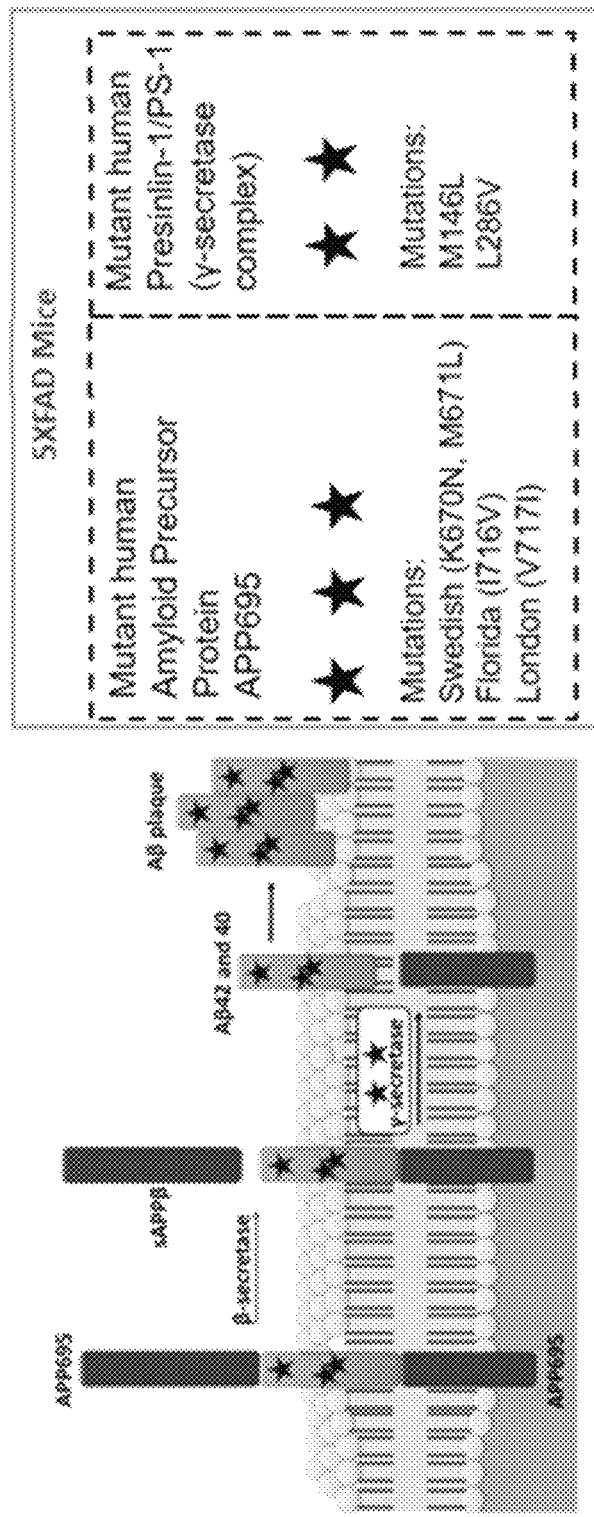
FIGS. 9A-9E. Schematic diagrams for genetic models of WT 5XFAD and ST3-deficient transgenic mice and comparison of observed phenotype and events of AD pathology in WT 5XFAD, ST3$^{-/-}$ 5 XFAD and LFA-treated WT 5XFAD mice.

Alzheimer's disease (AD) is a systemic neurodegenerative disorder of the central nervous system (CNS) that has a high prevalence in the aging population. The disease is associated with synaptic distinction, progressive loss of neurons, brain atrophy and progressive cognitive decline (Masters et al., 2015). An effective therapy for the disease has still not been developed (Graham et al., 2017; Selkoe and Hardy, 2016). Major hallmarks of the CNS pathology of AD include extracellular depositions of polymerized aggregated fragments of amyloid-β (Aβ) and intracellular fibrillary tangles. Polymeric and oligomeric AP species contribute to neuronal toxicity with subsequent neurodegeneration (Selkoe and Hardy, 2016). Neuronal amyloid precursor protein (APP) is expressed as a long transmembrane protein, which is cleaved by β-secretase and then by a γ-secretase complex consisting of four core proteins including presenilin (PS-1) into short peptides that stay on the cell surface (FIG. 9A) (Selkoe and Hardy, 2016). Known mutations in human APP (hAPP) and PS-1 genes are associated with increased aggregation of amyloid fragments and earlier onset of familial AD (FAD) (Shea et al., 2016). The mouse model of AD used in the study was 5XFAD transgenic mice that overexpress under neuronal Thy1 promoter three mutant hAPPs and two mutant PS-1 genes (FIG. 9B) (Oakley et al., 2006). These mice have extracellular amyloid depositions in the brain starting at 3 months of age and represent the most severe mouse model of AD (Oakley et al., 2006). Toxic fragments of human mutant APPs (e.g., $A\beta_{1-40}$ and $A\beta_{1-42}$ peptides) are present in the CNS of 5XFAD mice and have the ability to bind to neuronal lipid rafts (NLRs) (Hicks et al., 2012; Oakley et al., 2006).

Figure 9D:
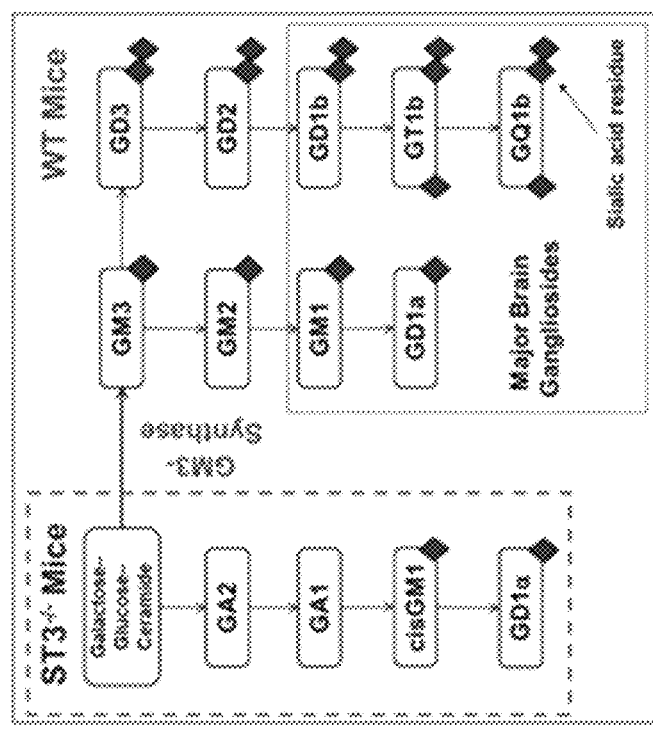
Figure 9C:
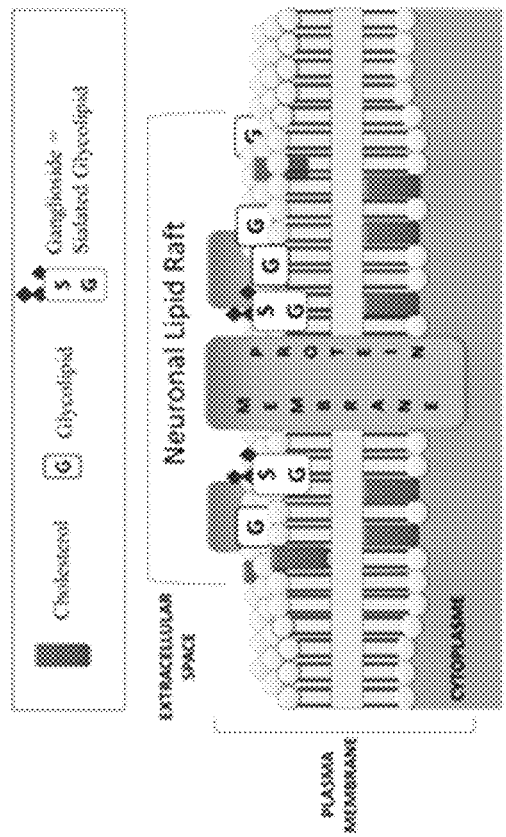

Neuronal membrane microdomains or NLRs are rigid parts of the plasma membranes of neuronal cells that are stabilized with intramembrane cholesterol and enriched with sialylated glycosphingolipids (gangliosides) and glycoproteins with sialic acid residues exposed to the surface (FIG. 9C) (Hicks et al., 2012). The areas of neuronal cells that are enriched with NLRs are post-synaptic density (PSD) membranes in neuronal synapses (Ponomarev, 2018; Suzuki et al., 2011). Gangliosides modulate the functions of receptors at post-synaptic membranes and the expression of gangliosides significantly changes during AD (Ariga et al., 2011; Hollmann and Seifert, 1986; Posse de Chaves and Sipione, 2010). Brain tissue is specifically enriched with sialylated gangliosides referred to as major brain gangliosides, including GM1, GD1a, GD1b, GT1b, and GQ1b (Sotnikov et al., 2013; Sturgill et al., 2012; Vajn et al., 2013). Sialylated gangliosides GM1, GD1a, GD1b, and GT1b account for 97% of all gangliosides in the human brain (Ando, 1983). These four gangliosides have the same core structure (Galβ1-3GalNAcβ1-4Galβ1-4Glcβ1-1'Cer), with one or two sialic acids attached to internal galactose in GM1 and GD1b, and an additional sialic acid on the terminal galactose of GD1a and GT1b (Yu et al., n.d.). It was previously discovered that gangliosides GM1, GD3, GT1b and GQ1b within NLR are recognized by platelets, leading to their degranulation and the secretion of pro-inflammatory factors and neurotransmitters that modulate the function of both neuronal and immune cells (Ponomarev, 2018; Sotnikov et al., 2013; Starossom et al., 2015). Ganglioside GM1 has been shown to be accumulated in patients with AD and to serve as a binding site for amyloid peptides, acting as a seed for Aβ aggregation (Yanagisawa, 2015). It was also demonstrated that inhibition of ganglioside synthesis via the inactivation of glucosylceramide synthase in neuronal cells resulted in decreased susceptibility of mouse cortical neurons to Aβ-induced toxicity (Herzer et al., 2016). It remains currently unclear, however, how Aβ binding to neuronal gangliosides contributes to disease pathology. The results of in vivo studies using hAPP transgenic animals that are partially deficient in certain gangliosides are contradictory. One study used 1XFAD transgenic mice that lack GM2-synthase (GM2S). These mice do not have gangliosides GM1, GD1a, GD1b, GT1b or GQ1b but do have GD3 and GM3. Surprisingly, they have an increased amyloid plaque burden in the CNS parenchyma and brain blood vessels (Oikawa et al., 2009). This demonstrates that the remaining GD3 and GM3 gangliosides exhibit compensatory upregulation and are still capable of promoting AD pathology. Another study used 2XFAD (hAPP/PS-1) mice with knockout of GD3-synthase (GD3S). These mice lack GD1b, GD3, GT1b and GQ1b but still have brain-abundant GM1, GD1a and GM3 gangliosides. In contrast to GM2S-deficient 1XFAD mice, GD3S-deficient 2XFAD mice showed an amelioration of AD pathology (Bernardo et al., 2009). Thus, the exact role of GM1 and the other major brain gangliosides GD3, GT1b and GQ1b in AD pathology remains controversial.

Figure 9E:
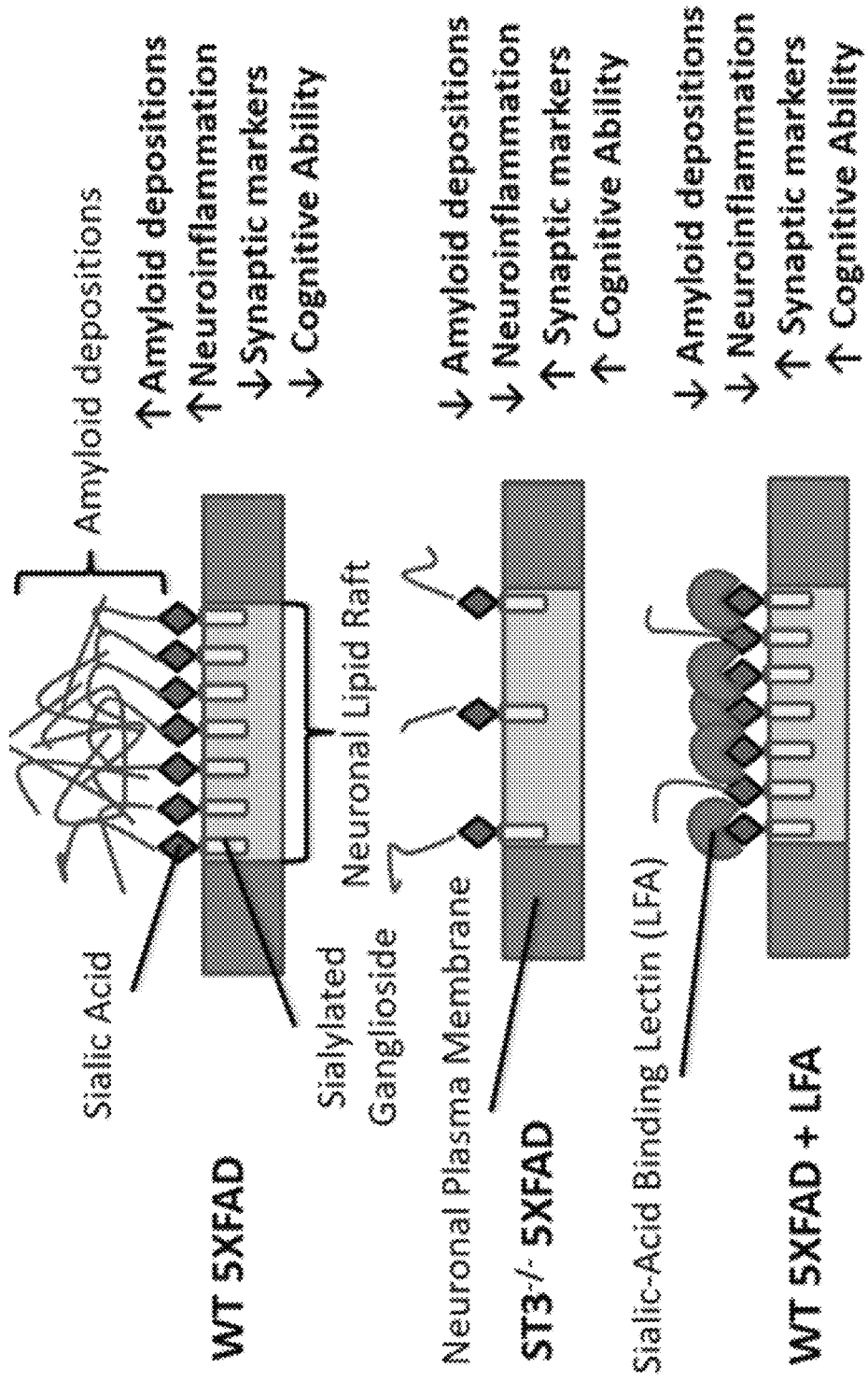

To understand the role of major brain gangliosides in AD pathology in vivo, 5XFAD mice were crossed with st3gal5-deficient (ST3$^{-/-}$) mice that lack GM3-synthase (α2,3-sialyltransferase), which is required for the synthesis of all major brain gangliosides in the CNS including GM1, GD1a, GD1b, GM3, GD3, GT1b and GQ1b (FIG. 9D) (Sturgill et al., 2012; Yoshikawa et al., 2009). It was found that 8-month-old ST3$^{-/-}$ 5XFAD mice had a significantly lower level of amyloid plaque burden when compared to a WT 5XFAD control group of the same age. Further analysis revealed that microglia actively phagocytized the amyloid plaques in these both groups. However, the increased numbers and a higher level of microglial cell activation were observed only in the brains of WT 5XFAD mice. Notably, ST3$^{-/-}$ 5XFAD mice did not display significant neuronal loss and they exhibited expression of synaptic markers and cognitive skills comparable to WT and ST3$^{-/-}$ mice without 5XFAD transgenes. Further treatment of 7-month-old WT 5XFAD mice with a sialic-acid binding lectin (*Limax flavus* agglutinin; LFA) that targets sialic acid on major brain gangliosides resulted in a decreased level of amyloid deposition, inhibited neuroinflammation, and elevated expression of synaptic markers with substantially improved cognitive functions. Thus, the findings in this study demonstrate that targeting brain-specific sialylated gangliosides is important for the amelioration of AD pathology and the maintenance of neuronal functions during aging (FIG. 9E).

Methods and Materials

Animals

Colonies of B6 (C57BL/6), and St3gal5-deficient (ST3$^{-/-}$) mice (Sotnikov et al., 2013) were maintained at the Laboratory Animal Service Centre (LASEC) of the Chinese University of Hong Kong (CUHK). ST3$^{-/-}$ mice were backcrossed to the B6 background for at least 12 generations. WT 5XFAD transgenic mice (B6.Cg-Tg(APPSwFlLon, PSEN1*M146L*L286V)6799Vas/Mmjax) were purchased from Jackson Laboratories and maintained at LASEC. For the experiments of this study, the present inventors crossed 5XFAD mice with ST3$^{-/-}$ mice to generate ST3$^{-/+}$ 5XFAD mice, which were then crossed with ST3$^{-/-}$ mice to generate ST3$^{-/-}$ 5XFAD mice. Mouse genotyping was performed by standard PCR according to the protocol provided by Jackson Laboratories. The study was performed in accordance with the recommendations of the ARRIVE guidelines (website: www.nc3rs.org.uk/arrive-guidelines). All animal protocols were approved by the Department of Health of the Government of Hong Kong and the Chinese University of Hong Kong Animal Experimentation Ethics Committee. For treatment with LFA, a group of WT 5XFAD mice received i.p. injections of 0.2 ml PBS or 0.2 ml of LFA (20 mg/kg) in PBS per mouse 3 times/week for 5 weeks, after which the Barnes maze cognitive test was performed and the animals were euthanized for histology and real-time RT PCR assays.

Histochemistry and Immunofluorescence

The 7-, 8-, or 12-month-old WT, ST3$^{-/-}$, WT 5XFAD, and ST3$^{-/-}$ 5XFAD mice were perfused with cold PBS, and then 1% paraformaldehyde in PBS. Their brains were dissected and fixed in 1% paraformaldehyde in PBS for 24 h, then dehydrated in 30% sucrose in PBS for 3-5 days, embedded in Tissue Tek (Sakura) and stored at −80° C. as in previous studies (Sotnikov et al., 2013). After this, 10-μm-thick frozen sections were prepared using Leica cryotome and stained for Congo red, or FITC conjugated Thioflavin T (ThT-FITC), or Cresyl violet (all from Sigma) with hematoxyline, and/or with DAPI (ThermoScientific) according to the standard protocols. For immunofluorescence, the sections were stained with goat antibodies for Iba1 (BioRad) combined with secondary anti-goat antibodies conjugated with AF594, or antibodies for β3-tubulin conjugated with AF488 (Millipore), or rabbit antibodies for the human APP (BioRad) combined with secondary anti-rabbit (Invitrogen) antibodies conjugated with AF594. A Carl Zeiss Axiophot-2 Microscope Integrated Biological Imaging System and confocal system with inverted microscope (Olympus FV1000) were used for imaging.

Flow Cytometry

The mice were perfused with PBS, and the brains were dissected, homogenized, and mononuclear cells were isolated using a 40%/70% Percoll gradient as described previously (Ponomarev et al., 2011; Veremeyko et al., 2012). Brain mononuclear cells were stained with anti-CD11b-AF488 (BD Biosciences), anti-Ly6C-PE (BD Biosciences), anti-CD45-APC-Cy7 (Biolegend), anti-CD86-AF647 (Biolegend) and anti-MHC class II-PerCP-Cy5.5 (Biolegend) antibodies and analyzed by 5-colour flow cytometry as previously described (Ponomarev et al., 2011; Sotnikov et al., 2013; Starossom et al., 2015; Veremeyko et al., 2018, 2012). Samples were analyzed using a BD LSRFortessa Flow Cytometer (BD Biosciences).

RNA Isolation and Real-Time RT PCR

For RNA isolation from brain tissue and cultured cells, the samples were homogenized and lysed using QIAzol Lysis Reagent (Qiagen) as described previously (Ponomarev et al., 2011; Veremeyko et al., 2012). RNA purification with DNase digestion was performed using a miRNeasy Mini Kit from Qiagen. Real-time RT PCR was performed using ABI ViiA 7 and ABI QuantStudio 7 (QS7) Flex Systems. For analysis of mRNA expression the following primers were used: PSD95 (forward 5'-TCTGTGCGAGAGGTAGCAGA-3' (SEQ ID NO: 1); reverse 5'-AAGCACTCCGTGAACTCCTG-3' (SEQ ID NO: 2)), Syn1α, (forward 5'-CCGCCAGCTGCCTTC-3' (SEQ ID NO: 3), reverse 5'-TGCAGCCCAATGACCAAA-3' (SEQ ID NO: 4)), IL-1β (forward 5'-CTTCCAGGAT-GAGGACATGAGCAC-3' (SEQ ID NO: 5), reverse 5'-TCATCATCCCATGAGTCACAGAGG-3' (SEQ ID NO: 6)), TNF (forward 5'-AGCCGATGGGTTGTACCTTG-3' (SEQ ID NO: 7), reverse 5'-GTGGGTGAG-GAGCACGTAGTC-3' (SEQ ID NO: 8)). Relative expression was calculated using the ΔCT method and normalized to the GADPH housekeeping gene (forward primer, 5'-ATGACCACAGTCCATGCCATC-3' (SEQ ID NO: 9); reverse primer, 5'-GAGCTTCCCGTTCAGCTCTG-3' (SEQ ID NO: 10)), and then the relative level of expression was calculated in comparison to control samples.

Barnes Maze Test

For the Barnes maze cognitive test, a white circular platform (92 cm in diameter) with 20 equally spaced holes (5 cm diameter; 7.5 cm between holes) was used according to a previously elaborated protocol described in the following shared online resource: website=nature.com/protocolexchange/protocols/349#. Groups of 3 to 5 mice were trained to locate a hole through which they could escape from the apparatus to an escape box during daily training sessions for 4 days. Latency to escape was scored manually on days 1-4. On day 5, a final trial was performed, in which the animals could not escape the apparatus and their latency time to finding the closed target hole and time spent in the area of the closed target hole was evaluated offline using Noldus Ethovision XT 11 software. Latency time was used as a measure of test performance in the final trial.

Statistical Analysis

The results are presented as bar graphs showing mean±S.E., or as whisker plots with median and 10%/90% percentiles, and the mean value indicated by a "+" symbol as indicated in figure legends. Unpaired Student's t-tests were used to determine significance between two experimental groups. P values of less than 0.05 were considered significant. SigmaPlot and GraphPad Prizm software were used to create the charts and perform statistical analysis.

Results

ST3-Deficient 5XFAD 8- and 12-Month-Old Mice have a Low Amyloid Plaque Burden and do not Exhibit Signs of Brain Atrophy.

It is known from the literature that WT 5XFAD mice start to exhibit widespread amyloid depositions in the cortex and decline in cognitive function at 4-6 months of age, while neuronal loss and a decrease in the expression of synaptic markers PSD95 and Syn-1 has been observed at 9-12 months (Oakley et al., 2006). Based on these data the inventors compared amyloid depositions in WT and ST3-deficient 5XFAD mice at 8 and 12 months of age when all manifestations of AD pathology were observed in the WT 5XFAD mice. It was observed that the density of amyloid plaques was 2-fold and 3-fold lower in the cortex of ST3$^{-/-}$ 5 XFAD mice when compared to WT 5XFAD mice of 8 and 12 months of age, respectively (FIG. 1A, D). Although amyloid plaques were still detected in very small numbers in ST3-deficient 5XFAD mice, these plaques were smaller and/or less dense as determined by Congo red staining (FIG. 1A). At 8 months of age the WT 5XFAD mice already exhibited clear signs of brain atrophy, which was manifested by a decrease in average brain weight when compared to age-matched WT control mice. Strikingly, 8-month-old ST3-deficient 5XFAD mice did not exhibit signs of brain atrophy and had average brain weights comparable to age-matched WT or ST3 control groups without FAD transgenes. These data reveal ameliorated AD pathology in ganglioside-deficient 5XFAD mice.

ST3-Deficient 5XFAD Mice do not Demonstrate Substantial Morphological Changes Associated with Activation of Microglia, but these Cells were Still Capable of Amyloid Phagocytosis.

Figures 2B, 2C:
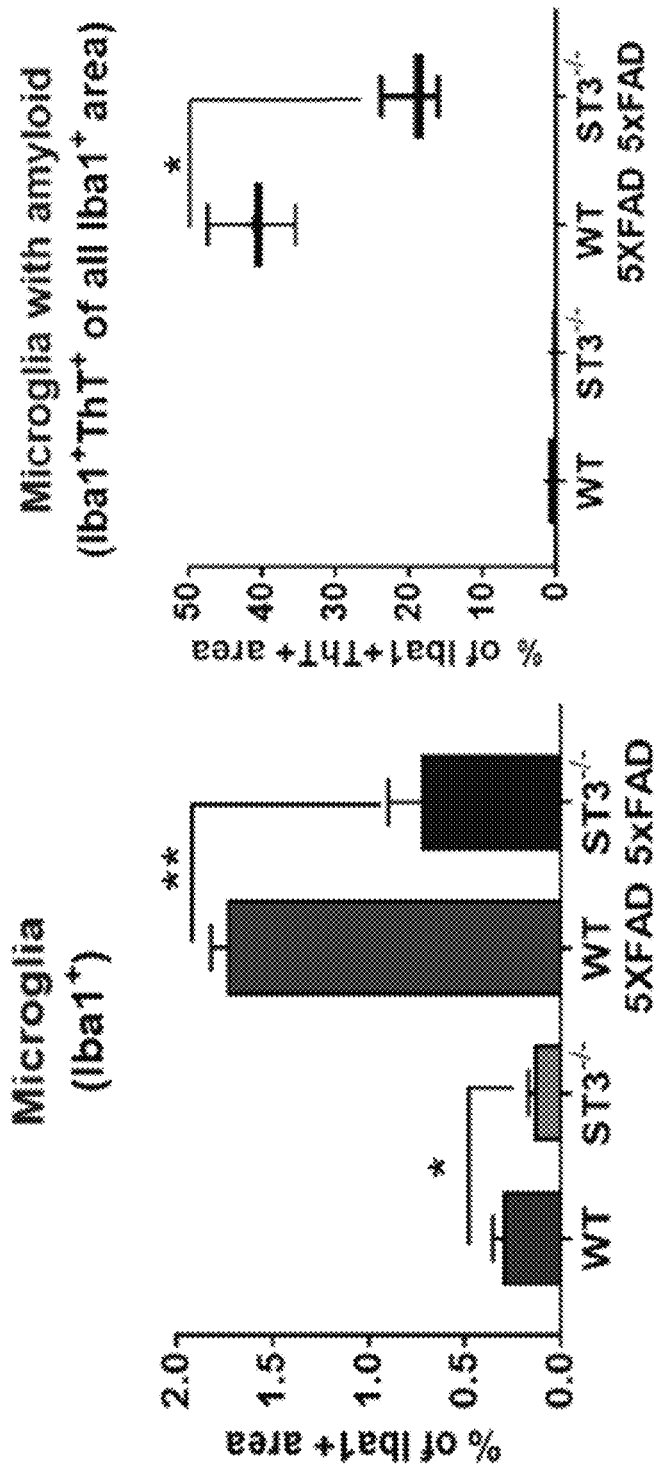

It is known that during AD, and in mouse models of the disease, microglia become activated and there is AD-associated neuroinflammation (Heneka et al., 2015; Sarlus and Heneka, 2017). Therefore, morphological changes associated with microglia activation and co-localization with amyloid deposits were evaluated in the cortex of 8-month-old WT 5XFAD and ST3$^{-/-}$ 5 XFAD mice (FIG. 2A; 5XFAD). Age-matched WT and ST3$^{-/-}$ mice without the FAD transgene were used as controls (FIG. 2A; No Transgene). It was observed that in the CNS of WT 5XFAD mice Iba1-positive microglial cells showed clear morphological signs of activation when compared with WT controls, as determined by the increases in cell size and cell number (FIG. 2A, 2B; WT 5XFAD). In contrast, ST3-deficient 5XFAD mice showed only mild signs of microglia activation when compared with ST3$^{-/-}$ controls as determined by the increases in cell size and cell number (FIG. 2A, 2B; ST3$^{-/-}$ 5 XFAD). In addition, the background level of microglia activation was lower in ST3$^{-/-}$ mice than in WT mice without the FAD transgene (FIG. 2B; WT and ST3$^{-/-}$). However, the microglia in ST3-deficient 5XFAD mice were still co-colorized with ThT-positive amyloid depositions, indicating on-going amyloid phagocytosis (FIG. 2A; ST3$^{-/-}$ 5 XFAD). In the WT 5XFAD mice, 40% of microglia were phagocytizing ThT-positive amyloid depositions, while 20% of microglia were phagocytizing amyloid depositions in the ST3-deficient 5XFAD mice (FIG. 2C). These data indicate that microglia were less activated in ST3$^{-/-}$ 5XFAD, but still capable of phagocytizing amyloid depositions.

Figures 3C, 3D:
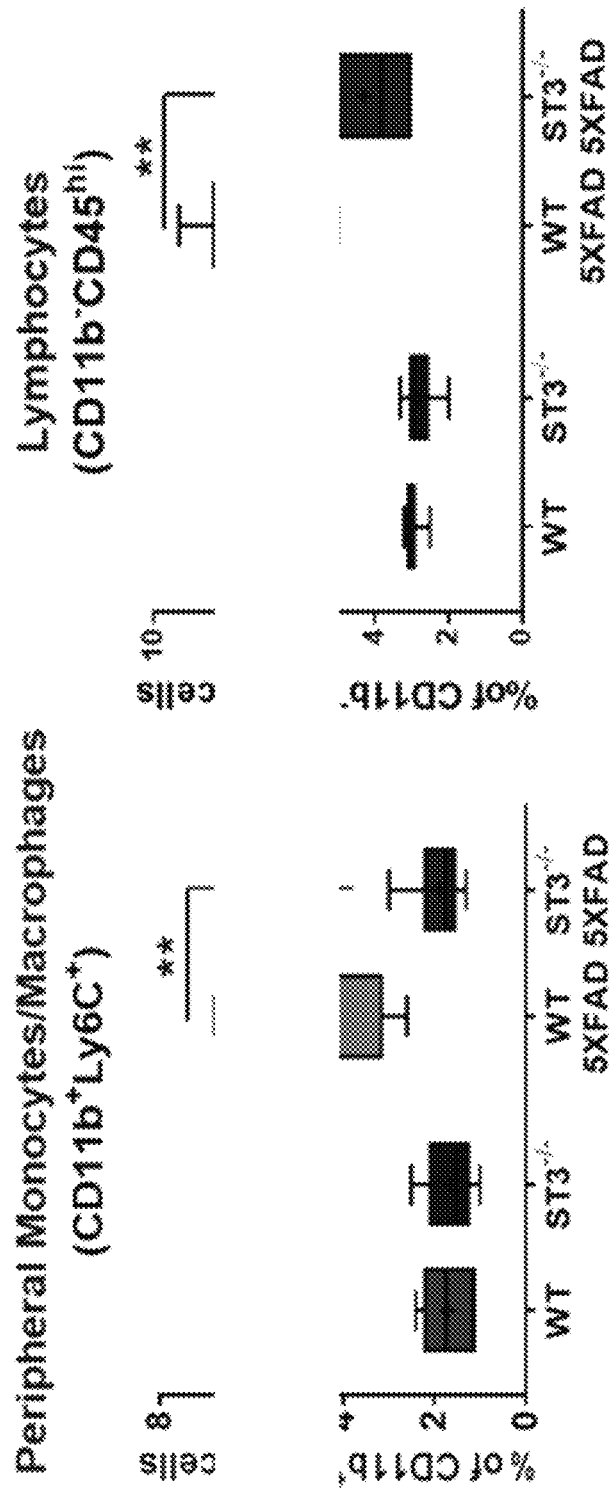

ST3-Deficient 5XFAD Mice have Low Levels of Monocyte and Lymphocyte Infiltration in the CNS During neuroinflammation other Iba1-positive cells, such as peripheral monocytes/macrophages, may be present in the CNS of 8-month-old 5XFAD mice (Ponomarev et al., 2005). The extent of infiltration of peripheral monocytes/macrophages and lymphocytes was therefore evaluated in the WT, ST3$^{-/-}$, WT 5XFAD, and ST3$^{-/-}$ 5 XFAD mice using multicolor flow cytometry to analyze the expression of CD11b, Ly6C, and CD45. According to previous studies, peripheral monocytes can be determined in the CNS as CD11b$^+$Ly6C$^+$ cells, while lymphocytes can be determined as CD11b$^+$CD45 cells, and microglia are represented by CD11b$^+$CD45$^{low/int}$Ly6C– cells (Mayo et al., 2014; Ponomarev et al., 2005). It was discovered that in the WT and ST3$^{-/-}$ mice peripheral monocytes constituted 1-2% of all brain mononuclear cells, while in the WT 5XFAD mice their number increased to an average of 4% but remained close to 2% in the ST3$^{-/-}$ 5 XFAD mice (FIG. 3A, 3C). Lymphocytes were present in the WT and ST3-deficient mice at a level of 2-3% of all brain mononuclare cells, while their level was increased to an average of 7% in the 5XFAD mice and to 4% in ST3-deficient 5XFAD mice (FIG. 3B, 3D). Thus, the levels of peripheral monocytes and lymphocytes were found to be low in the WT, ST3$^{-/-}$, WT FAD and ST3$^{-/-}$ FAD mice; and the levels of peripheral monocytes and lymphocytes were reduced 2-fold in the CNS of ST3-deficient 5XFAD mice when compared to WT 5XFAD animals.

Microglia from ST3-Deficient 5XFAD Mice have a Low Level of Expression of Activation Markers MHC Class II and CD86

Figures 4C, 4D:
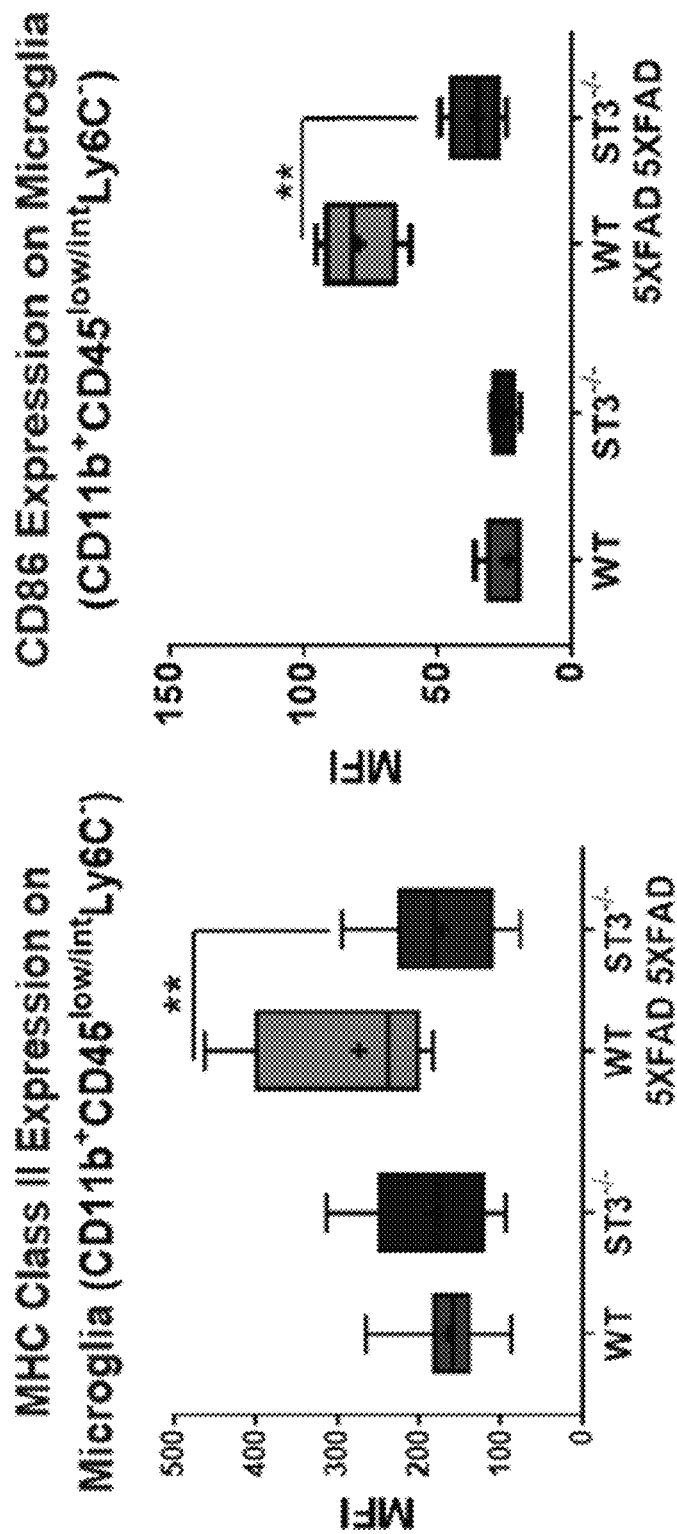

The extent of activation of microglia was further investigated. To exclude peripheral monocytes/macrophages, CD11b$^+$CD45$^{low/int}$Ly6 C$^-$ gated cells (FIG. 3A, B) were analyzed for the expression of known activation markers for microglia MHC class II (FIGS. 4A, 4C) and CD86 (FIGS. 4B, 4D). Both activation markers were upregulated in the WT 5XFAD mice when compared to the WT controls, while in the ST3$^{-/-}$ 5 XFAD mice the expression of MHC class II and CD86 decreased 2-fold to levels comparable to WT or ST3$^{-/-}$ controls (FIGS. 4A-4D). Thus, the levels of expression of MHC class II and CD86 on microglia were significantly reduced in the CNS of ST3-deficient 5XFAD mice.

Figure 5A:
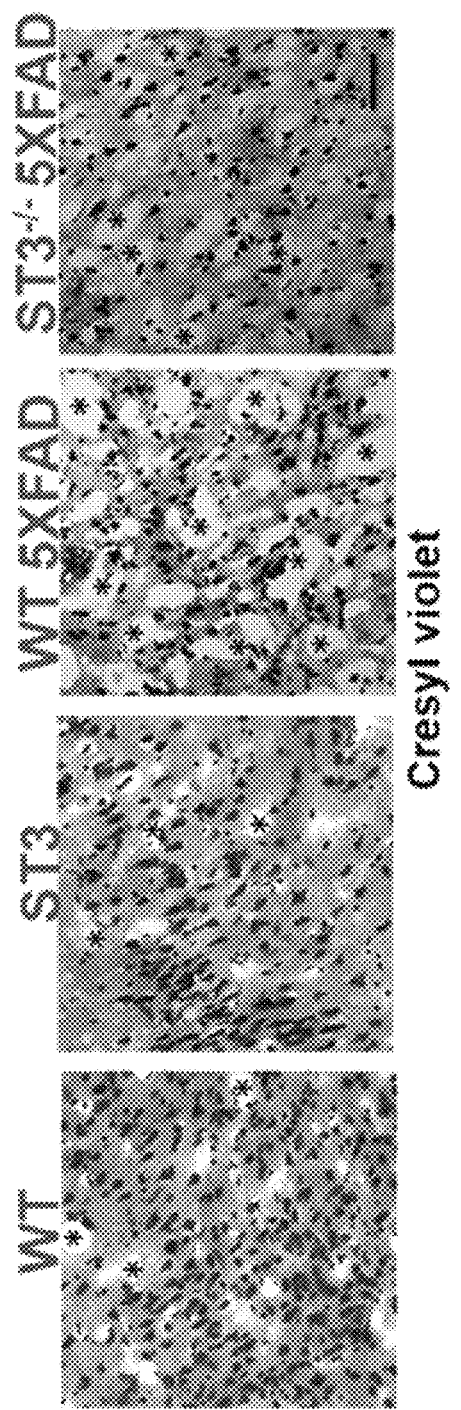
FIGS. 5A-5D. Analysis of extent of amyloid-related neuronal damage and atrophy in the brain cortex of WT 5XFAD and ST3$^{-/-}$ 5 XFAD mice.
Figure 5B:
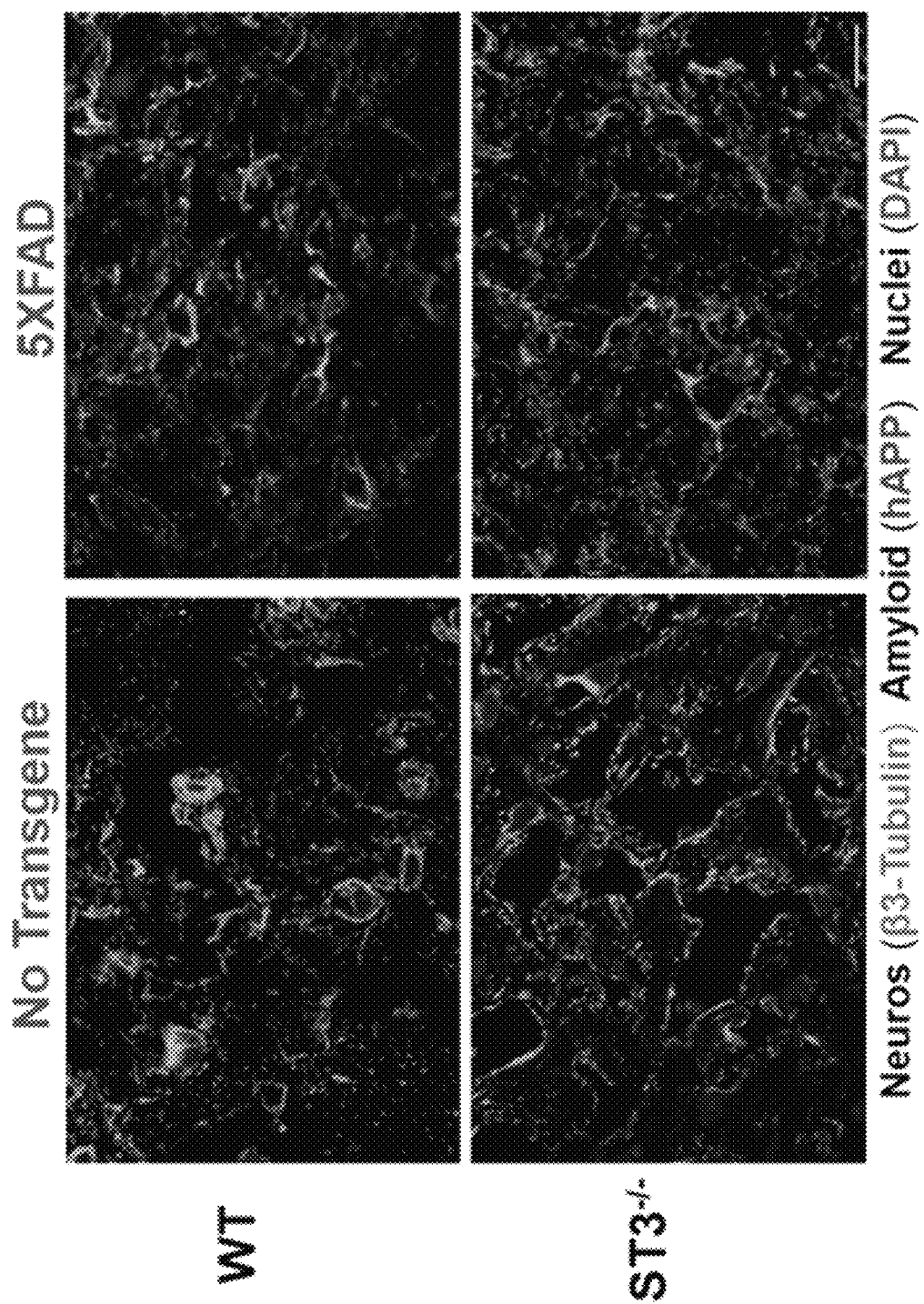
Figures 5C, 5D:
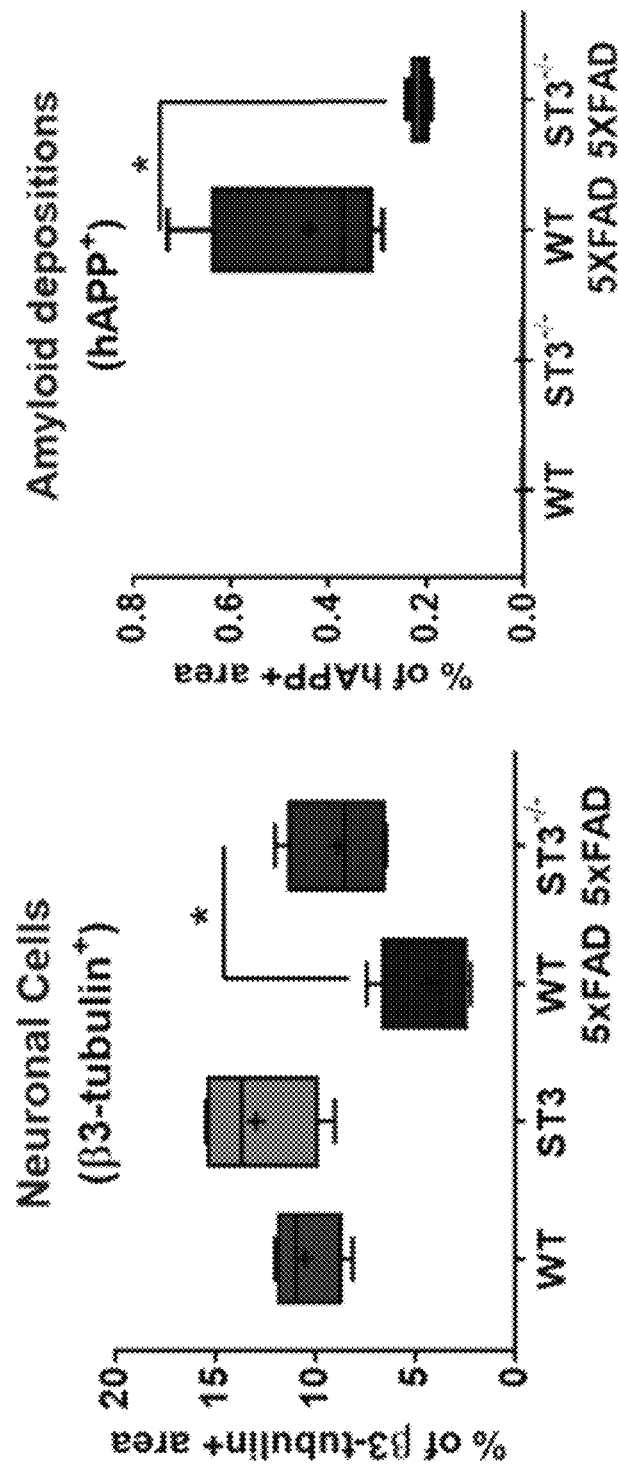

ST3-Deficient 5XFAD Mice do not Exhibit Neuronal Loss and have Very Low Levels of Amyloid Deposition in the Brain It was observed that the WT 5XFAD mice exhibited signs of brain atrophy as determined by a decrease in brain weight (FIG. 1C) (Peters, 2006). Another sign of atrophy and cognitive decline is an increase in the volume of the perivascular space (Favaretto et al., 2017; Zhang et al., 2016). Using Cresyl violet staining, an increased volume of perivascular space in the cortex of the WT 5XFAD mice was found compared to the WT and ST3$^{-/-}$ controls. The increase in the volume of the perivascular space was much less evident in the ST3$^{-/-}$ 5 XFAD mice (FIG. 5A). To further evaluate neuronal loss in the area of amyloid depositions accumulation, the neuronal marker β3-tubulin and human APP were stained for. It was revealed that neuronal loss was evident in hAPP-positive areas of the WT 5XFAD mice but not the ST3$^{-/-}$ 5 XFAD mice (FIG. 5B, C). It was confirmed that hAPP load was significantly lower in the areas of amyloid deposition in the ST3$^{-/-}$ 5 XFAD mice when compared to WT 5XFAD mice (FIG. 5D). These findings demonstrate that ST3-deficient mice do not exhibit substantial neuronal loss in the areas of amyloid deposition.

ST3-Deficient 5XFAD Mice do not Exhibit Downregulated Pro-Inflammatory Cytokines IL-1β and TNF but have Upregulated Synaptic Markers PSD95 and Syn-1

Figure 6B:
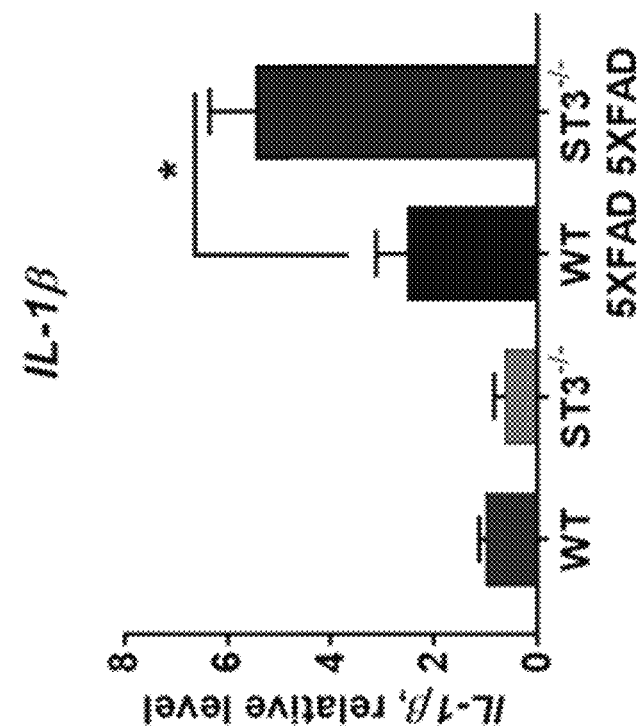
Figure 6A:
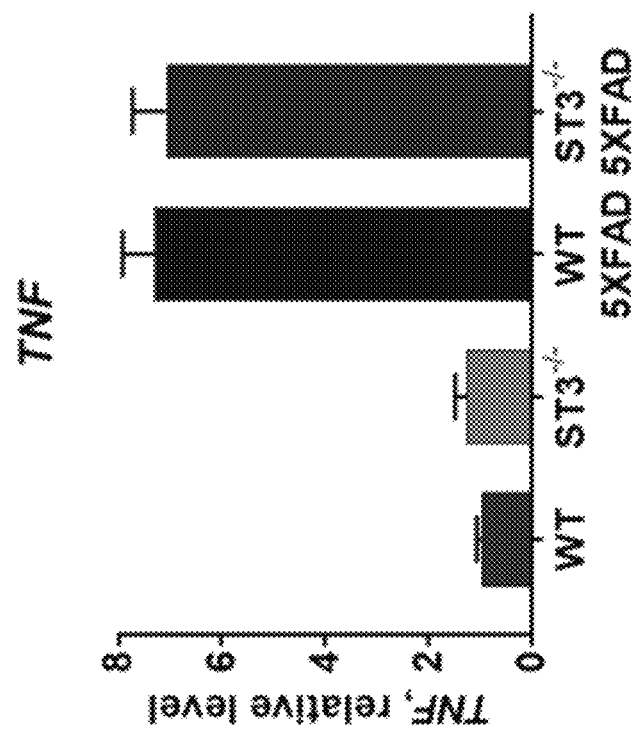

In addition to assessing the infiltration of peripheral leukocytes, microglia activation, and neuronal loss, the expression of two main pro-inflammatory cytokines, TNF and IL-1β, and two main synaptic markers, PSD95 and Syn1α, was examined. As expected, both TNF and IL-1β were upregulated in the WT 5XFAD mice when compared to the control WT group (Boza-Serrano et al., 2018; Landel et al., 2014). However, the expression of TNF in the ST3$^{-/-}$ 5 XFAD mice was at the same level as in the WT 5XFAD mice, while expression of IL-1β was elevated ~2-fold (FIG. 6A, 6B).

Expression of PSD95 and Syn1α was reported to be decreased in 9-month-old WT 5XFAD mice (Oakley et al., 2006). This was confirmed for 8-month-old WT 5XFAD mice, in which both markers were decreased when compared to the WT controls (FIG. 6C, 6D; WT and WT 5XFAD). The expression of both markers was elevated in the ST3$^{-/-}$ mice when compared to the WT mice (FIG. 6C, 6D; WT and ST3$^{-/-}$), and stayed high in the ST3$^{-/-}$ 5 XFAD mice (FIG. 6C, 6D; ST3$^{-/-}$ 5 XFAD). These data demonstrate that in contrast to the WT 5XFAD mice, the level of synaptic markers was not downregulated in the ST3$^{-/-}$ 5 XFAD mice.

Figures 6E, 6F:
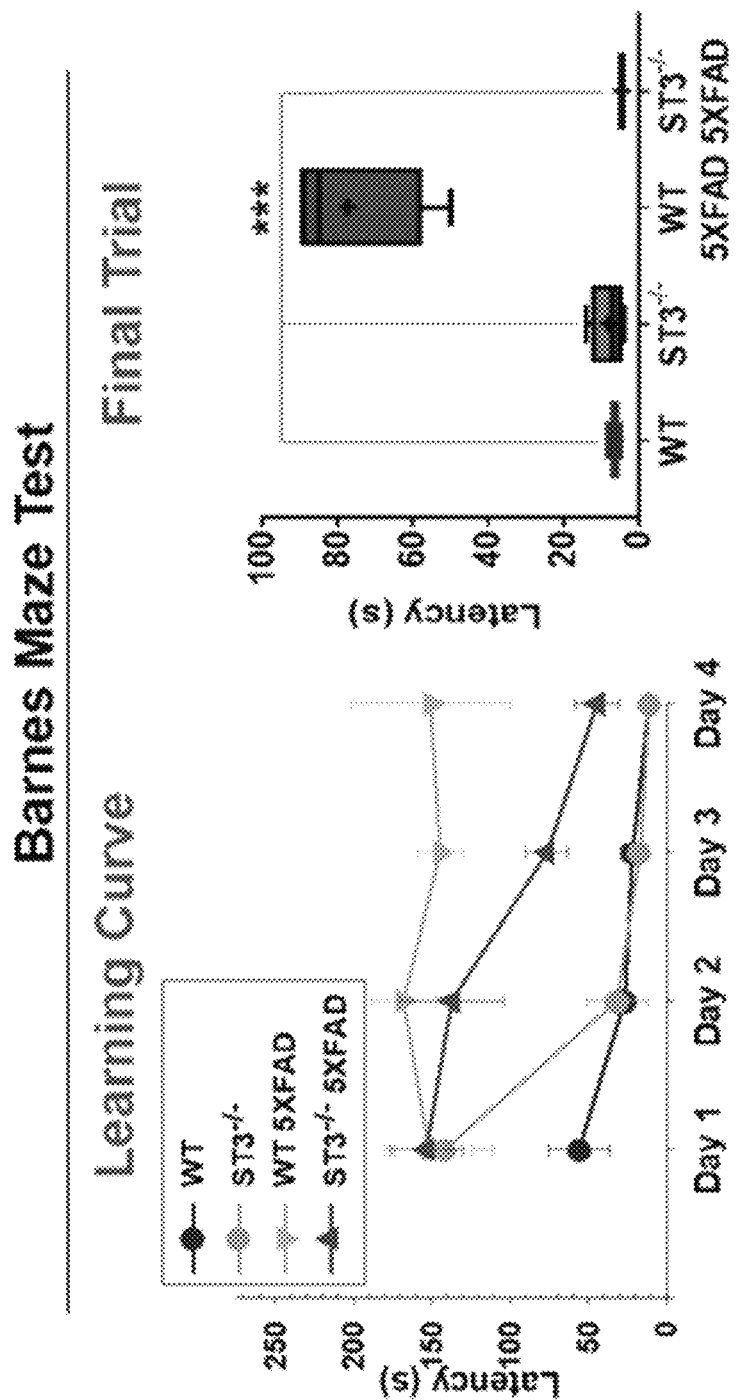

The Cognitive Performance of ST3-Deficient 5XFAD Mice is Comparable to that of WT Controls As the ST3-deficient 5XFAD mice had a low level of amyloid depositions, did not demonstrate significant neuronal loss, and had normal levels of synaptic markers, it was expected that these mice would have intact cognitive abilities. To test this, a Barnes maze test that measures spatial learning and memory (Rosenfeld and Ferguson, 2014) was used. Interestingly, on day 1 of training only the WT mice had good performance, while the ST3-deficient mice showed the same delayed learning process as the WT 5XFAD and ST3$^{-/-}$ 5XFAD mice (FIG. 6E; Day 1). On day 2 of training, the ST3-deficient mice showed the same performance as the WT mice, while the 3$^{-/-}$ 5 XFAD mice still had a similar performance to the WT 5XFAD mice (FIG. 6E; Day 2). On day 3, the performance of the ST3-deficient 5XFAD, but not the WT 5XFAD mice, was significantly improved and reached a level close to that of the WT mice by day 4 (FIG. 6E; Day 3 and Day 4). In the final trial on day 5, the performance of the ST3$^{-/-}$ 5 XFAD mice was comparable to that of the WT and ST3$^{-/-}$ controls (FIG. 6F). These results demonstrate that the ST3-deficient 5XFAD mice had spatial and memory functions comparable to the WT controls.

Figure 7A:
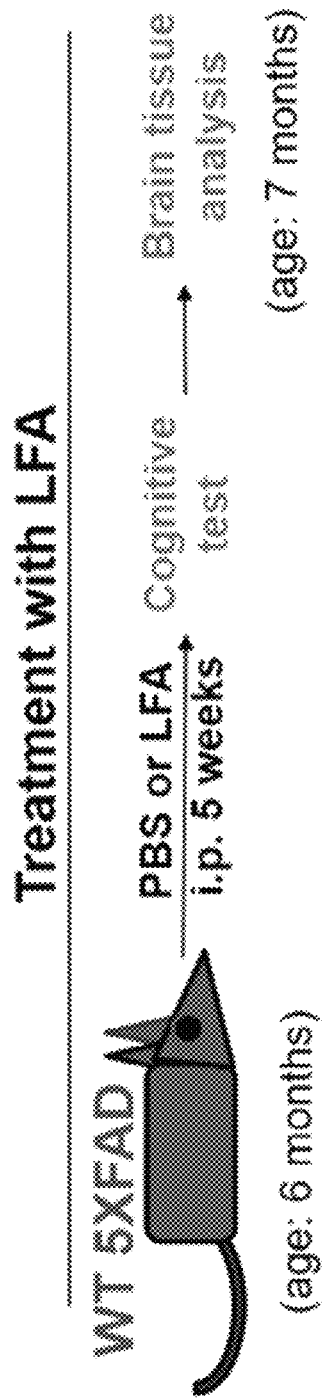
Figures 7B, 7C:
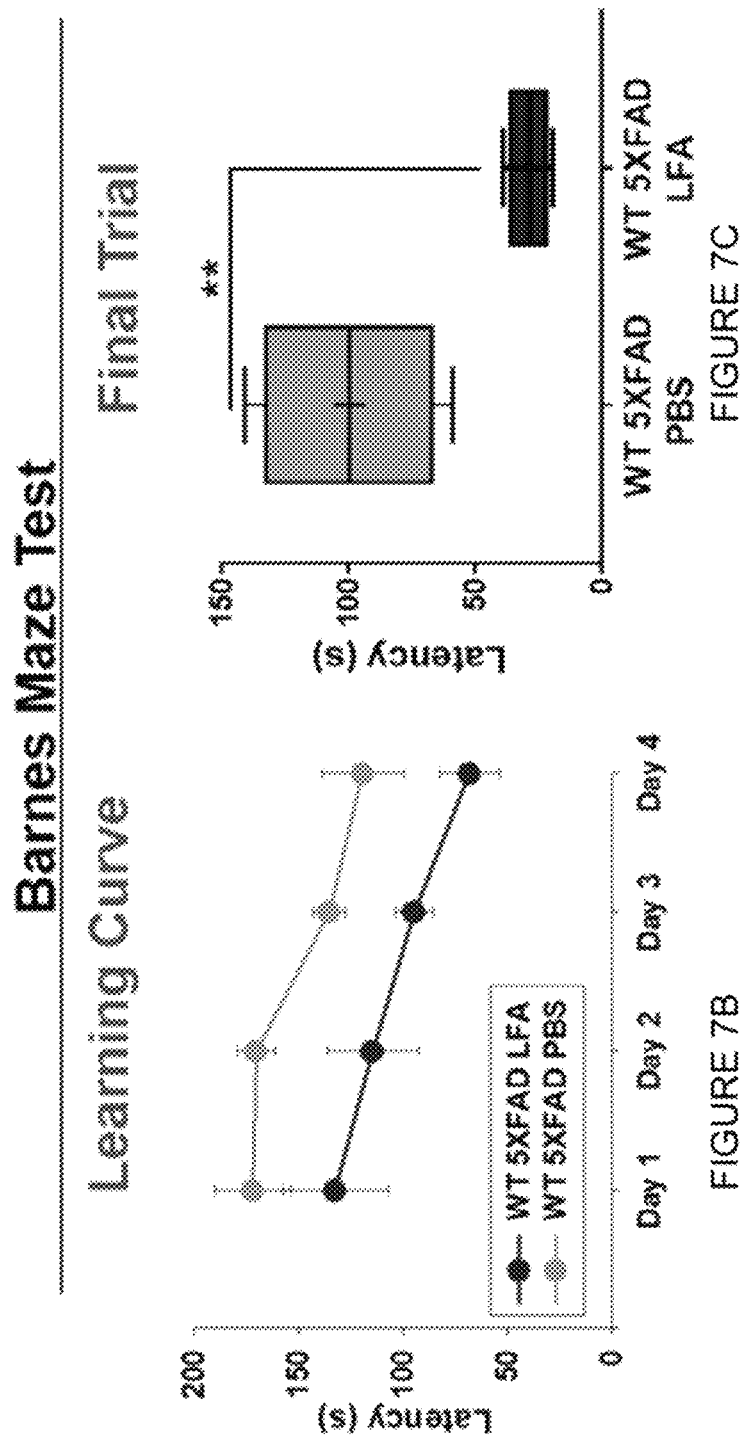
Figures 8A, 8B:
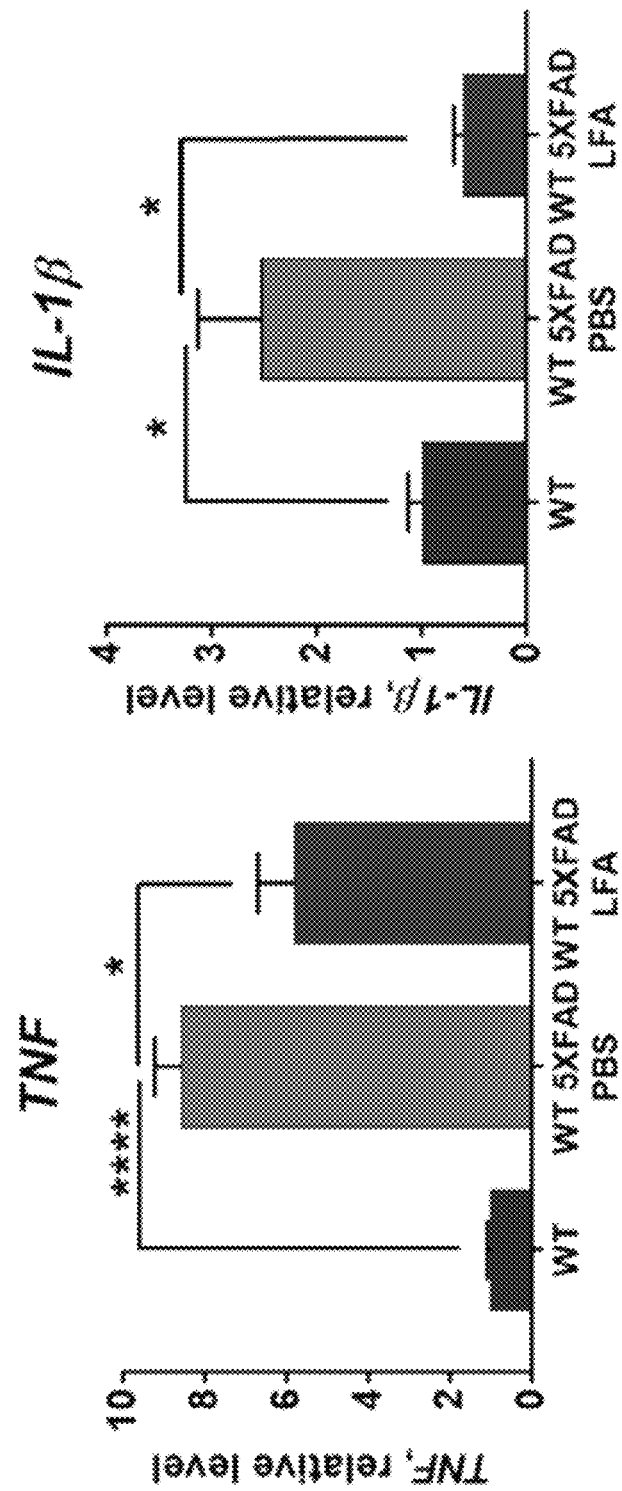
FIGS. 8A-8E. Effect of administration of sialic acid-specific lectin LFA on the level of neuroinflammation in WT 5XFAD mice.
Figure 8C:
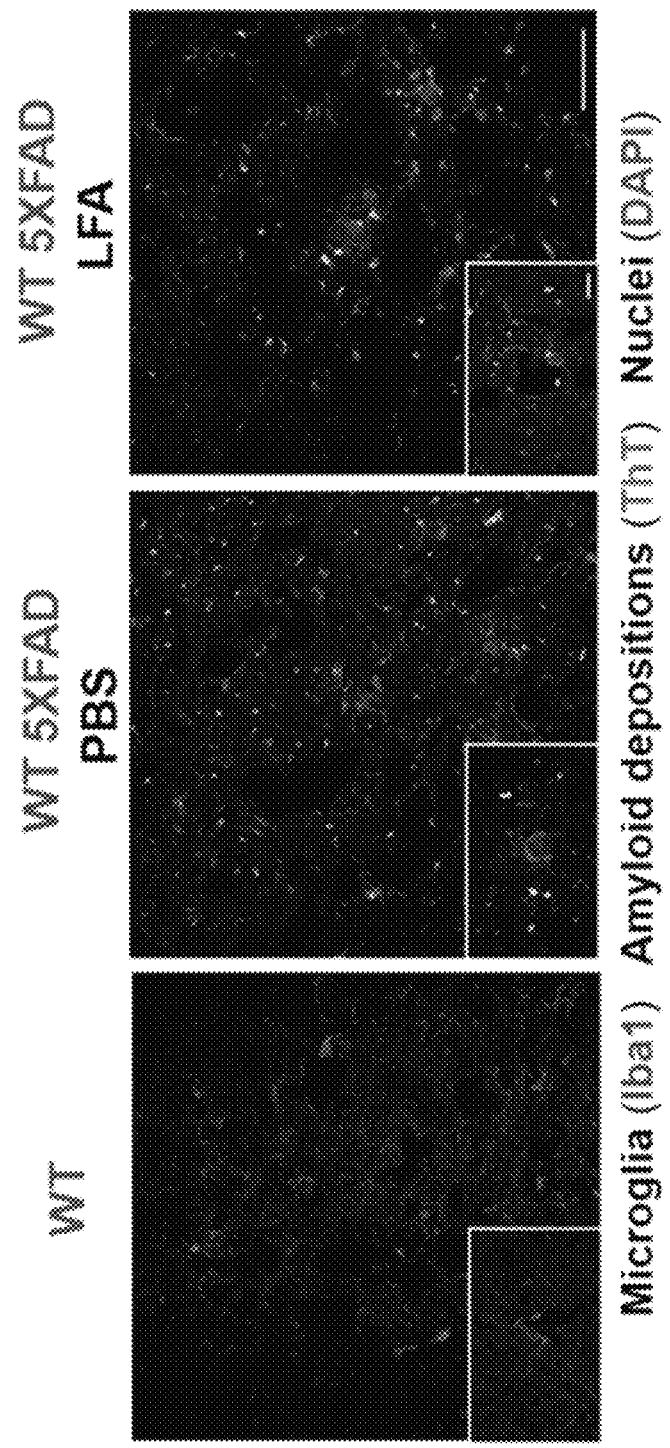
Figure 8E:
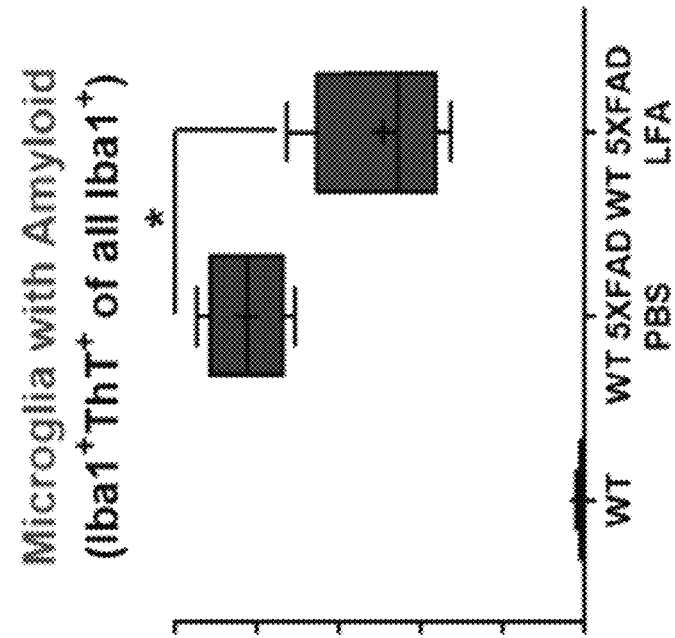
Figure 8D:
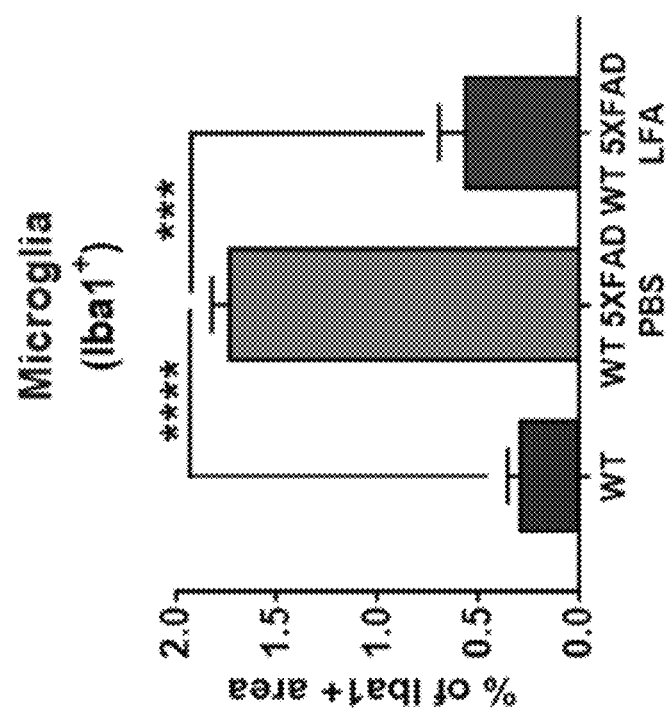

Treatment of WT 5XFAD Mice with Sialic Acid-Specific Lectin Results in Improved Performance on the Cognitive Test, Decreased Amyloid Depositions, Normalized Expression of Synaptic Markers, and Reduced Neuroinflammation As the absence of major brain sialylated gangliosides in the ST3-deficient mice was associated with significantly improved AD pathology, it was hypothesized that targeting the surface of sialylated gangliosides may be beneficial for AD. It is known that sialic acid is exposed to the outer surface of glycolipids and glycoproteins (Varki, 2008). Moreover, sialic acid has been shown to be critical for the binding of amyloid peptides to brain gangliosides (Ariga et al., 2001). In the CNS, 75% of total sialic acid mass belongs to gangliosides (Schnaar et al., 2014). Therefore, there is the possibility of blocking sialylated acid on the surface of gangliosides using sialic-acid specific lectins. *Limax flavus* agglutinin (LFA) lectin specifically binds to sialic acid and has a low level of toxicity (Knibbsso et al., 1993; Sotnikov et al., 2013). Treatment was stated for 6-month-old WT 5XFAD, which are known to have distinct symptoms of AD as determined by definitive cognitive problems by the age of 6 months (Oakley et al., 2006). 6-month-old WT 5XFAD mice were treated with i.p. injection of LFA 3 times a week for 1 month. The cognitive test was then administered, to compare the functional results with pathology analysis of brain tissues (FIG. 7A). Significantly improved performance was found in the LFA- vs. PBS-treated WT 5XFAD mice on days 3 and 4 of training (FIG. 7B) and in the final trial (FIG. 7C). When the cortical areas of these mice were analyzed, a significant decrease in amyloid plaque burden was found in the LFA-treated WT 5XFAD mice (FIG. 7D, 7E). LFA treatment significantly upregulated expression of PSD95 and Syn1α to levels exceeding those of the WT controls and similar to those of the ST3$^{-/-}$ mice (FIG. 7F, 7G). Treatment of the WT 5XFAD mice with LFA decreased expression of TNF 1.5-fold and expression of IL-β 3-fold (FIG. 8A, 8B). Similarly, LFA treatment decreased activation of microglia (FIG. 8C, 8D) and the percentage of microglia associated with amyloid depositions (FIG. 8C, 8E). These findings demonstrate that treatment of WT 5XFAD mice with LFA significantly ameliorated AD pathology and neuroinflammation.

DISCUSSION

In this study, the role of brain sialylated gangliosides was investigated in AD pathology in a 5XFAD mouse model with overexpression of human mutated APP and PS1 genes. It was found that 5XFAD mice that lack all major brain gangliosides had significantly reduced levels of amyloid depositions and decreased levels of both neurodegeneration and CNS inflammation. Moreover, treating the WT 5XFAD mice with a sialic-specific lectin for one month resulted in significant improvement of AD pathology as determined by decreased levels of amyloid depositions and neuroinflammation and upregulated synaptic markers and significantly improved cognitive abilities. Notably, LFA treatment resulted in a similar phenotype to that observed in ST3-deficient 5XFAD mice (FIG. 9E).

Gangliosides share the same structure and composition in all mammals from humans to rodents (Yu et al., n.d.). Therefore, in contrast to protein targets, which are often not structurally identical between mammalian species, the targeting of gangliosides can be modeled in mice or in in vitro model membrane systems. It was shown on human autopsy brain sections that at early stages of AD GM1 serves as a binding site for amyloid fragments to become a new center (seed) for aggregation (Yanagisawa, 2015). It is notable that GM1-bound amyloid-β was found in early stages of AD, because it was not found in patients with advanced AD (Yanagisawa et al., 1995). A more recent study conducted in a mouse model of AD confirmed that amyloid oligomeric peptides bind to neuronal GM1 in vivo, but was not clear whether and how such binding contributes to AD pathology (Hong et al., 2014). Studies that inhibited glucosylceramide synthase (GCS) demonstrated that mouse cortical and hippocampal neurons become less susceptible to amyloid toxicity possibly by modulating expression of the insulin receptor, which is important for neuronal survival and functions (Herzer et al., 2016; Pomytkin et al., 2018). These studies suggested that the binding of amyloid fragments to gangliosides contributes to neurodegeneration and possibly to the progression of AD, but did not provide definitive proof in vivo.

Further in vitro studies on model membrane systems demonstrated that $A\beta_{1-40}$ peptides do not bind to single GM1 gangliosides but rather to rigid GM1 clusters in membrane domains stabilized by cholesterol (Kakio et al., 2001). These membrane domains with ganglioside clusters and cholesterol are known to be resistant to mild detergents such as 0.5% Triton X-100 and are referred to as lipid rafts. Experiments with model membranes with modified GM1 demonstrated that amyloid peptide $A\beta_{1-40}$ binds efficiently to lyso-GM1, which lacks one fatty acid chain, indicating that the hydrophilic part of gangliosides is more important for binding than the fatty acid chain (Utsumi et al., 2009). In support of this, it was shown that binding of amyloid peptides $A\beta_{1-40}$ and $A\beta_{1-42}$ to asialo-GM1 was greatly reduced or completely inhibited (Ariga et al., 2001; Choo-Smith et al., 1997; Hong et al., 2014; Williamson et al., 2006). It was shown that $A\beta_{1-42}$ has a better ability to bind sialylated gangliosides than does less toxic $A\beta_{1-40}$ (Ariga et al., 2001), and the major brain poly-sialylated gangliosides GQ1b, GT1b, and GD3 have a better ability to bind amyloid peptides than mono-sialylated GM1 or GD1a. These studies suggest a critical role for sialic acid connected to internal galactose on a carbohydrate core for amyloid peptide binding to major brain gangliosides; however sialic acid connected to terminal galactose could also contribute to this binding (Ariga et al., 2001 (Ariga et al., 2011). In support of this, treatment of primary cultured hippocampal neurons with neuraminidase that removes sialic acid from the surface of lipid rafts significantly decreased the level of neurotoxicity of $A\beta_{1-42}$ (Malchiodi-Albedi et al., 2010; Wang et al., 2001). Moreover, removal of the cholesterol that stabilizes neuronal lipid rafts also decreased amyloid-induced neurotoxicity (Wang et al., 2001). Also, it was shown in acute hippocampal brain slice cultures that blocking the GM1 sialic acid with Cholera toxin subunit B (CTB) decreases Aβ peptide oligomer-mediated LTP inhibition (Hong et al., 2014). These in vitro data demonstrate the importance of sialylated gangliosides within neuronal lipid rafts for the binding of amyloid fragments to neurons, which in turn causes neurotoxicity and decreases in neuronal synaptic activity. These studies explain why the ST3-deficient and LFA-treated 5XFAD mice in our experiments had significantly ameliorated AD pathology (FIG. 9E).

Neuronal lipid rafts play an important role in normal and pathological CNS functions (Hicks et al., 2012; Simons and Ehehalt, 2002). In neurons, lipid rafts are present mostly in mature neurons in neurites and synapses and in the areas containing neurotrophic receptors such as TrkB (Tsui-Pierchala et al., 2002). Lipid rafts are also present in astroglial cells in the adult brain, and are integral part of structures of bloodbrain barrier (BBB). (Sotnikov et al., 2013). It was previously revealed that neuronal lipid rafts are directly recognized by platelets that become degranulated and produce a number of pro-inflammatory factors important for the development of autoimmune CNS inflammation (Ponomarev, 2018; Sotnikov et al., 2013; Starossom et al., 2015). In AD pathology, glycolipid composition and the function of neuronal lipid rafts change as the disease progresses (Ariga et al., 2011). It has been shown that in humans GM1 and GM2 are accumulated in AD, while in 2XFAD mice with overexpression of hAPP/PS-1 there is an accumulation of GQ1bα and GT1α, which have the highest capacity to bind amyloid peptides (Ariga et al., 2001, 2010; Pernber et al., 2012). This study indicates that the sialylated gangliosides GM1, GM2, GM3, GD1a, GD1b, GD2, GD3, GT1b, and GQ1b, which are absent in ST3-deficient mice, play a key role in the development of AD pathology. However, ST3-deficient mice still have sialylated gangliosides cisGM1 (GM1b) and GD1α (Yoshikawa et al., 2009; Yu et al., n.d.). In contrast to major brain gangliosides, GM1b and GD1α do not have internal galactose with sialic acid, which is critical for the binding of amyloid peptides (Ariga et al., 2001; Yu et al., n.d.). However, both GM1b and GD1α have terminal galactose with sialic acid, which contribute to binding of amyloid peptides. Importantly, GD1α has sialic acid connected to GalNac, which significantly enhances the binding of amyloid peptides (Ariga et al., 2001). Ganglioside GD1α is not expressed in WT mice, but it is found in ST3-deficient mice (Yoshikawa et al., 2009). Thus, ST3-deficient mice could still have binding sites for amyloid peptides, especially GD1α, which is the likely mediator of the residual AD pathology found in the $ST3^{-/-}$ 5XFAD mice in this study.

Two previous studies have investigated the role of particular gangliosides in vivo in mouse models of AD. The first study used mice lacking GM2-synthase that were crossed with 1XFAD mice that overexpress hAPP with Swedish and London mutations (Oikawa et al., 2009). These mice still express GD3, GM3, and GT3 but do not have GM1, GM2, GD1a, GD1b, GD2, GT1b, GQ1b, cisGM1 or GD1α. Interestingly, GM2S$^{-/-}$ 1 XFAD mice showed a significant increase in amyloid depositions in the CNS parenchyma and areas of CNS blood vessels with exacerbation of the disease (Oikawa et al., 2009). These results are not that surprising because these mice express GT3 and have a very high level of GD3 expression in blood vessels (Matsuda et al., 2006; Wen et al., 1999). The second study used GD3-synthase-deficient mice crossed with 2XFAD mice that overexpressed hAPP with a Swedish mutation and mutated human PS-1 gene. GD3S-deficient 2XFAD mice do not have GD2, GD3, GD1b, GT1b, or GQ1b but they still have the sialylated gangliosides GM1, GM2, GM3, GD1a, cisGM1 and GD1α. Moreover, the levels of GM1 and GD2 are significantly increased in these mice (Bernardo et al., 2009). Similar to our ST3$^{-/-}$ 5XFAD mice that only had cisGM1 and GD1α, it was found that GD3S$^{-/-}$ 2 XAPP mice had reduced levels of amyloid depositions and improved cognitive abilities (Bernardo et al., 2009). These results are quite surprising as GM1 has been shown in a number of in vivo and in vitro studies to be critical for Aβ binding (Yanagisawa, 2015). The observed decrease in AD pathology in these mice might be explained by the mild model of AD in 2XFAD mice when compared to 5XFAD mice, the most robust model of AD. GT1b and GQ1b may be more important for AD pathology than GM1, at least in mouse models. However, GM1 has been shown to be very important in human AD. It is believed that depending on the disease severity, the targeting of one or several brain gangliosides may be an effective AD therapy. In early stages of the disease, the targeting of GT1b or GQ1b alone may be sufficient as these gangliosides have a high affinity for Aβ peptides.

To further verify the importance of targeting sialylated gangliosides in vivo, WT 5XFAD mice were treated with the sialic-specific lectin LFA. It was observed that LFA, which specifically binds sialic acid regardless of its linkage to carbohydrates (Knibbsso et al., 1993), was more potent in reducing the expression of pro-inflammatory cytokines TNF and IL-1β, which were not reduced in the ST3-deficient 5XFAD mice. This is because LFA has broader specificity when compared to genetic elimination of gangliosides in ST3-deficient mice that still express sialylated gangliosides GM1b and GD1α (Yoshikawa et al., 2009). It was previously found that LFA effectively inhibited autoimmune neuroinflammation in a mouse model of experimental autoimmune encephalomyelitis, indicating its strong anti-inflammatory properties (Sotnikov et al., 2013). Thus, LFA has a potential double action to reduce amyloid depositions and inhibit AD-related neuroinflammation.

Microglia activation, infiltration of peripheral leukocytes, and upregulation of pro-inflammatory cytokines have been shown to be manifestations of AD-related neuroinflammation (Heneka et al., 2015; Sarlus and Heneka, 2017). The studies in ST3-deficient 5XFAD mice demonstrated that the level of microglia activation was reduced as determined by expression of MHC class II and CD86. Infiltration of peripheral monocytes and lymphocytes was very low in WT 5XFAD mice, indicating the major role of microglia activation in this model. However, infiltration of peripheral leukocytes was still significantly reduced in ST3-deficient FAD mice. These findings also indicated that microglia in ST3-deficient mice still underwent morphological changes of activation and were capable of amyloid phagocytosis. TNF was not reduced in ST3-deficient mice and the expression of IL-1β was even elevated. This could indicate that these cytokines are produced by other cell types (e.g. astrocytes) in ST3-deficient 5XFAD mice, or that microglia in these mice still produce high levels of pro-inflammatory cytokines. The role of pro-inflammatory cytokines in AD pathology remains controversial. On the one hand, cytokine IL-1β contributes to AD pathology (Griffin and Mrak, 2002). On the other hand, cytokine TNF has been shown to be beneficial in AD (Montgomery et al., 2011). The results of this study clearly show that ameliorated AD pathology is associated with a decrease in microglia activation markers MHC class II and CD86, but not pro-inflammatory cytokines, in ST3-deficient mice. However, when mice were treated with LFA, TNF and IL-1β expression was reduced, as well as microglia activation. This implies that the extent of AD-related CNS inflammation is reduced when the disease is ameliorated.

Thus, the findings reported here demonstrate the effectiveness of LFA treatment, which significantly decreased amyloid depositions in the brain, possibly by binding to sialylated gangliosides in neuronal lipid rafts and preventing the binding of amyloid peptides. LFA treatment also inhibited neuroinflammation more effectively than deletion of the st3gal5 gene. It is clear that LFA is quite a broad-spectrum agent binding to sialic acid on different gangliosides and glycoproteins in the CNS and periphery. However, in the CNS more that 80% of all glycans belong to glycolipids and 75% of sialic acid belongs to gangliosides (Schnaar et al., 2014). Thus, it is believed that in these experiments LFA mostly targeted brain gangliosides, reaching 80% of their targets in the brain. Although LFA does not demonstrate 100% specificity, it is believed that the results discussed here highlight a very promising approach to specifically target sialylated brain-specific gangliosides such as GT1b or GQ1b that are expressed mostly in the brain. This approach has the potential to develop highly specific and efficient AD therapy in the future.

All patents, patent applications, and other publications, including GenBank Accession Numbers, cited in this application are incorporated by reference in the entirety for all purposes.

REFERENCES

Ando, S., 1983. Gangliosides in the nervous system. Neurochem. Int. 5, 507-537.

Ariga, T., Kobayashi, K., Hasegawa, A., Kiso, M., Ishida, H., Miyatake, T., 2001. Characterization of High-Affinity Binding between Gangliosides and Amyloid (β-Protein. Arch. Biochem. Biophys. 388, 225-230.

Ariga, T., Wakade, C., Yu, R. K., 2011. The pathological roles of ganglioside metabolism in Alzheimer's disease: effects of gangliosides on neurogenesis. Int. J. Alzheimers. Dis. 2011, 193618.

Ariga, T., Yanagisawa, M., Wakade, C., Ando, S., Buccafusco, J. J., McDonald, M. P., Yu, R. K., 2010. Ganglioside Metabolism in a Transgenic Mouse Model of Alzheimer's Disease: Expression of Chol-1α Antigens in the Brain. ASN Neuro 2, AN20100021.

Bernardo, A., Harrison, F. E., McCord, M., Zhao, J., Bruchey, A., Davies, S. S., Jackson Roberts, L., Mathews, P. M., Matsuoka, Y., Ariga, T., Yu, R. K., Thompson, R., McDonald, M. P., 2009. Elimination of GD3 synthase improves memory and reduces amyloid-β plaque load in transgenic mice. Neurobiol. Aging 30, 1777-1791.

Boza-Serrano, A., Yang, Y., Paulus, A., Deierborg, T., 2018. Innate immune alterations are elicited in microglial cells before plaque deposition in the Alzheimer's disease mouse model 5xFAD. Sci. Rep. 8, 1550.

Choo-Smith, L. P., Garzon-Rodriguez, W., Glabe, C. G., Surewicz, W. K., 1997. Acceleration of amyloid fibril formation by specific binding of Abeta-(1-40) peptide to ganglioside-containing membrane vesicles. J. Biol. Chem. 272, 22987-90.

Favaretto, A., Lazzarotto, A., Riccardi, A., Pravato, S., Margoni, M., Causin, F., Anglani, M. G., Seppi, D., Poggiali, D., Gallo, P., 2017. Enlarged Virchow Robin spaces associate with cognitive decline in multiple sclerosis. PLoS One 12, e0185626.

Graham, W. V., Bonito-Oliva, A., Sakmar, T. P., 2017. Update on Alzheimer's Disease Therapy and Prevention Strategies. Annu. Rev. Med. 68, 413-430.

Griffin, W. S. T., Mrak, R. E., 2002. Interleukin-1 in the genesis and progression of and risk for development of neuronal degeneration in Alzheimer's disease. J. Leukoc. Biol. 72, 233-8.

Heneka, M. T., Carson, M. J., Khoury, J. El, Landreth, G. E., Brosseron, F., Feinstein, D. L., Jacobs, A. H., Wyss-Coray, T., Vitorica, J., Ransohoff, R. M., Herrup, K., Frautschy, S. A., Finsen, B., Brown, G. C., Verkhratsky, A., Yamanaka, K., Koistinaho, J., Latz, E., Halle, A., Petzold, G. C., Town, T., Morgan, D., Shinohara, M. L., Perry, V. H., Holmes, C., Bazan, N. G., Brooks, D. J., Hunot, S., Joseph, B., Deigendesch, N., Garaschuk, O., Boddeke, E., Dinarello, C. A., Breitner, J. C., Cole, G. M., Golenbock, D. T., Kummer, M. P., 2015. Neuroinflammation in Alzheimer's disease. Lancet Neurol. 14, 388-405.

Herzer, S., Meldner, S., Rehder, K., Grone, H.-J., Nordstrom, V., 2016. Lipid microdomain modification sustains neuronal viability in models of Alzheimer's disease. Acta Neuropathol. Commun. 4, 103.

Hicks, D. A., Nalivaeva, N. N., Turner, A. J., 2012. Lipid Rafts and Alzheimer's Disease: Protein-Lipid Interactions and Perturbation of Signaling. Front. Physiol. 3, 189.

Hollmann, M., Seifert, W., 1986. Gangliosides modulate glutamate receptor binding in rat brain synaptic plasma membranes. Neurosci. Lett. 65, 133-8.

Hong, S., Ostaszewski, B. L., Yang, T., O'Malley, T. T., Jin, M., Yanagisawa, K., Li, S., Bartels, T., Selkoe, D. J., 2014. Soluble Aβ Oligomers Are Rapidly Sequestered from Brain ISF In Vivo and Bind GM1 Ganglioside on Cellular Membranes. Neuron 82, 308-319.

Kakio, A., Nishimoto, S. I., Yanagisawa, K., Kozutsumi, Y., Matsuzaki, K., 2001. Cholesterol-dependent formation of GM1 ganglioside-bound amyloid beta-protein, an endogenous seed for Alzheimer amyloid. J. Biol. Chem. 276, 24985-90.

Knibbsso, R. N., Osbornell, S. E., Glickll, G. D., Goldstein$, I. J., 1993. Binding Determinants of the Sialic Acid-specific Lectin from the Slug *Limax flavus*. J. Biol. Chem. 268, 18524-18531.

Landel, V., Baranger, K., Virard, I., Loriod, B., Khrestchatisky, M., Rivera, S., Benech, P., Féron, F., 2014. Temporal gene profiling of the 5XFAD transgenic mouse model highlights the importance of microglial activation in Alzheimer's disease. Mol. Neurodegener. 9, 33.

Malchiodi-Albedi, F., Contrusciere, V., Raggi, C., Fecchi, K., Rainaldi, G., Paradisi, S., Matteucci, A., Santini, M. T., Sargiacomo, M., Frank, C., Gaudiano, M. C., Diociaiuti, M., 2010. Lipid raft disruption protects mature neurons against amyloid oligomer toxicity. Biochim. Biophys. Acta-Mol. Basis Dis. 1802, 406-415.

Masters, C. L., Bateman, R., Blennow, K., Rowe, C. C., Sperling, R. A., Cummings, J. L., 2015. Alzheimer's disease. Nat. Rev. Dis. Prim. 1, 15056.

Matsuda, J., Vanier, M. T., Popa, I., Portoukalian, J., Suzuki, K., 2006. GD3- and O-acetylated GD3-gangliosides in the GM2 synthase-deficient mouse brain and their immunohistochemical localization. Proc. Jpn. Acad. Ser. B. Phys. Biol. Sci. 82, 189-96.

Mayo, L., Trauger, S. A., Blain, M., Nadeau, M., Patel, B., Alvarez, J. I., Mascanfroni, I.D., Yeste, A., Kivisäkk, P., Kallas, K., Ellezam, B., Bakshi, R., Prat, A., Antel, J. P., Weiner, H. L., Quintana, F. J., 2014. Regulation of astrocyte activation by glycolipids drives chronic CNS inflammation. Nat. Med. 20, 1147-1156.

Montgomery, S. L., Mastrangelo, M. A., Habib, D., Narrow, W. C., Knowlden, S. A., Wright, T. W., Bowers, W. J., 2011. Ablation of TNF-RI/RII Expression in Alzheimer's Disease Mice Leads to an Unexpected Enhancement of Pathology. Am. J. Pathol. 179, 2053-2070.

Oakley, H., Cole, S. L., Logan, S., Maus, E., Shao, P., Craft, J., Guillozet-Bongaarts, A., Ohno, M., Disterhoft, J., Van Eldik, L., Berry, R., Vassar, R., 2006. Intraneuronal beta-Amyloid Aggregates, Neurodegeneration, and Neuron Loss in Transgenic Mice with Five Familial Alzheimer's Disease Mutations: Potential Factors in Amyloid Plaque Formation. J. Neurosci. 26, 10129-10140.

Oikawa, N., Yamaguchi, H., Ogino, K., Taki, T., Yuyama, K., Yamamoto, N., Shin, R.-W., Furukawa, K., Yanagisawa, K., 2009. Gangliosides determine the amyloid pathology of Alzheimer's disease. Neuroreport 20, 1.

Pernber, Z., Blennow, K., Bogdanovic, N., Mansson, J.-E., Blomqvist, M., 2012. Altered Distribution of the Gangliosides GM1 and GM2 in Alzheimer's Disease. Dement. Geriatr. Cogn. Disord. 33, 174-188.

Peters, R., 2006. Ageing and the brain. Postgrad. Med. J. 82, 84-8.

Pomytkin, I., Costa-Nunes, J. P., Kasatkin, V., Veniaminova, E., Demchenko, A., Lyundup, A., Lesch, K.-P., Ponomarev, E. D., Strekalova, T., 2018. Insulin receptor in the brain: Mechanisms of activation and the role in the CNS pathology and treatment. CNS Neurosci. Ther.

Ponomarev, E. D., Shriver, L. P., Maresz, K., Dittel, B. N., 2005. Microglial cell activation and proliferation precedes the onset of CNS autoimmunity. J. Neurosci. Res. 81, 374-389.

Ponomarev, E. D., Veremeyko, T., Barteneva, N., Krichevsky, A. M., Weiner, H. L., 2011. MicroRNA-124 promotes microglia quiescence and suppresses EAE by deactivating macrophages via the C/EBP-α-PU.1 pathway. Nat. Med. 17, 64-70.

Ponomarev, E. D. E. D., 2018. Fresh evidence for platelets as neuronal and innate immune cells: their role in the activation, differentiation and deactivation of Th1, Th17 and Tregs during tissue inflammation. Front. Immunol. 9, 406.

Posse de Chaves, E., Sipione, S., 2010. Sphingolipids and gangliosides of the nervous system in membrane function and dysfunction. FEBS Lett. 584, 1748-1759.

Rosenfeld, C. S., Ferguson, S. A., 2014. Barnes maze testing strategies with small and large rodent models. J. Vis. Exp. e51194.

Sarlus, H., Heneka, M. T., 2017. Microglia in Alzheimer's disease. J. Clin. Invest. 127, 3240-3249.

Schnaar, R. L., Gerardy-Schahn, R., Hildebrandt, H., 2014. Sialic acids in the brain: gangliosides and polysialic acid in nervous system development, stability, disease, and regeneration. Physiol. Rev. 94, 461-518.

Selkoe, D. J., Hardy, J., 2016. The amyloid hypothesis of Alzheimer's disease at 25 years. EMBO Mol. Med. 8, 595-608.

Shea, Y.-F., Chu, L.-W., Chan, A. O.-K., Ha, J., Li, Y., Song, Y.-Q., 2016. A systematic review of familial Alzheimer's disease: Differences in presentation of clinical features among three mutated genes and potential ethnic differences. J. Formos. Med. Assoc. 115, 67-75.

Simons, K., Ehehalt, R., 2002. Cholesterol, lipid rafts, and disease. J. Clin. Invest. 110, 597-603.

Sotnikov, I., Veremeyko, T., Starossom, S. C., Barteneva, N., Weiner, H. L., Ponomarev, E. D., 2013. Platelets Recognize Brain-Specific Glycolipid Structures, Respond to Neurovascular Damage and Promote Neuroinflammation. PLoS One 8, e58979.

Starossom, S. C., Veremeyko, T., Yung, A. W. Y. Y., Dukhinova, M., Au, C., Lau, A. Y., Weiner, H. L., Ponomarev, E. D., 2015. Platelets play differential role during the initiation and progression of autoimmune neuroinflammation. Circ. Res. 117, 779-792.

Sturgill, E. R., Aoki, K., Lopez, P. H. H., Colacurcio, D., Vajn, K., Lorenzini, I., Majić, S., Yang, W. H., Heffer, M., Tiemeyer, M., Marth, J. D., Schnaar, R. L., 2012. Biosynthesis of the major brain gangliosides GD1a and GT1b. Glycobiology 22, 1289-1301.

Suzuki, T., Zhang, J., Miyazawa, S., Liu, Q., Farzan, M. R., Yao, W.-D., 2011. Association of membrane rafts and postsynaptic density: proteomics, biochemical, and ultrastructural analyses. J. Neurochem. 119, 64-77.

Tsui-Pierchala, B. A., Encinas, M., Milbrandt, J., Johnson, E. M., 2002. Lipid rafts in neuronal signaling and function. Trends Neurosci. 25, 412-7.

Utsumi, M., Yamaguchi, Y., Sasakawa, H., Yamamoto, N., Yanagisawa, K., Kato, K., 2009. Up-and-down topological mode of amyloid β-peptide lying on hydrophilic/hydrophobic interface of ganglioside clusters. Glycoconj. J. 26, 999-1006.

Vajn, K., Viljetić, B., Degmečić, I. V., Schnaar, R. L., Heffer, M., 2013. Differential Distribution of Major Brain Gangliosides in the Adult Mouse Central Nervous System. PLoS One 8, e75720.

Varki, A., 2008. Sialic acids in human health and disease. Trends Mol. Med. 14, 351-60.

Veremeyko, T., Starossom, S.-C., Weiner, H. L., Ponomarev, E. D., 2012. Detection of MicroRNAs in Microglia by Real-time PCR in Normal CNS and During Neuroinflammation. J. Vis. Exp. 65, e4097.

Veremeyko, T., Yung, A. W. Y., Dukhinova, M., Kuznetsova, I. S., Pomytkin, I., Lyundup, A., Strekalova, T., Barteneva, N. S., Ponomarev, E. D., 2018. Cyclic AMP pathway suppress autoimmune neuroinflammation by inhibiting functions of encephalitogenic CD4 T cells and enhancing M2 macrophage polarization at the site of inflammation. Front. Immunol. 9.

Wang, S. S., Rymer, D. L., Good, T. A., 2001. Reduction in cholesterol and sialic acid content protects cells from the toxic effects of beta-amyloid peptides. J. Biol. Chem. 276, 42027-34.

Wen, F. Q., Jabbar, A. A., Patel, D. A., Kazarian, T., Valentino, L. A., 1999. Atherosclerotic aortic gangliosides enhance integrin-mediated platelet adhesion to collagen. Arterioscler. Thromb. Vasc. Biol. 19, 519-524.

Williamson, M. P., Suzuki, Y., Bourne, N. T., Asakura, T., 2006. Binding of amyloid β-peptide to ganglioside micelles is dependent on histidine-13. Biochem. J. 397, 483-490.

Yanagisawa, K., 2015. GM1 ganglioside and Alzheimer's disease. Glycoconj. J. 32, 87-91.

Yanagisawa, K., Odaka, A., Suzuki, N., Ihara, Y., 1995. GM1 ganglioside-bound amyloid beta-protein (A beta): a possible form of preamyloid in Alzheimer's disease. Nat. Med. 1, 1062-6.

Yoshikawa, M., Go, S., Takasaki, K., Kakazu, Y., Ohashi, M., Nagafuku, M., Kabayama, K., Sekimoto, J., Suzuki, S.-i., Takaiwa, K., Kimitsuki, T., Matsumoto, N., Komune, S., Kamei, D., Saito, M., Fujiwara, M., Iwasaki, K., Inokuchi, J. -i., 2009. Mice lacking ganglioside GM3 synthase exhibit complete hearing loss due to selective degeneration of the organ of Corti. Proc. Natl. Acad. Sci. 106, 9483-9488.

Yu, R. K., Tsai, Y.-T., Ariga, T., Yanagisawa, M., n.d. Structures, biosynthesis, and functions of gangliosides—An overview.

Zhang, X., Ding, L., Yang, L., Qin, W., Yuan, J., Li, S., Hu, W., 2016. Brain Atrophy Correlates with Severe Enlarged Perivascular Spaces in Basal Ganglia among Lacunar Stroke Patients. PLoS One 11, e0149593.

---

What is claimed is:

1. A method for treating Alzheimer's disease, comprising administering to a patient in need thereof an effective amount of a composition consisting essentially of *Limax flavus* agglutinin (LFA) and a physiologically acceptable excipient.

2. The method of claim 1, wherein the administering step comprises injection, oral ingestion, or nasal inhalation.

3. The method of claim 2, wherein the administering step comprises intravenous, intramuscular, intraperitoneal, or subcutaneous injection.

4. The method of claim 3, wherein LFA is administered by intravenous injection in an amount of about 5-100 mg/kg patient body weight.

5. The method of claim 4, wherein LFA is administered by intravenous injection in an amount of about 20 mg/kg patient body weight.

* * * * *